United States Patent
Finkbeiner

(10) Patent No.: US 7,139,415 B2
(45) Date of Patent: Nov. 21, 2006

(54) ROBOTIC MICROSCOPY SYSTEMS

(75) Inventor: Steven M. Finkbeiner, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 818 days.

(21) Appl. No.: 10/313,942

(22) Filed: Dec. 5, 2002

(65) Prior Publication Data

US 2003/0103662 A1 Jun. 5, 2003

Related U.S. Application Data

(60) Provisional application No. 60/337,585, filed on Dec. 5, 2001.

(51) Int. Cl.
*G06K 9/00* (2006.01)

(52) U.S. Cl. .................... 382/128; 382/274; 250/201.3

(58) Field of Classification Search ................ 382/103, 382/107, 128–134, 153, 168, 191, 194, 203, 382/209, 232, 255, 260, 274, 286, 305; 435/6, 435/7.1; 359/390; 250/201.4, 201.3; 422/102; 356/601; 378/20
See application file for complete search history.

(56) References Cited

U.S. PATENT DOCUMENTS

| | | | |
|---|---|---|---|
| 4,000,417 A * | 12/1976 | Adkisson et al. | ........ 250/201.4 |
| 4,012,112 A | 3/1977 | Masterson | |
| 4,232,970 A | 11/1980 | Sawamura et al. | |
| 4,513,438 A | 4/1985 | Graham et al. | |
| 4,705,949 A | 11/1987 | Grimes, II et al. | |
| 4,810,869 A | 3/1989 | Yabe et al. | |
| 4,833,382 A | 5/1989 | Gibbs | |
| 4,920,053 A | 4/1990 | Inoue et al. | |
| 4,958,920 A | 9/1990 | Jorgens et al. | |
| 4,974,952 A | 12/1990 | Focht | |
| 5,073,857 A | 12/1991 | Peters et al. | |
| 5,231,279 A | 7/1993 | Nakamura | |
| 5,473,706 A | 12/1995 | Bacus et al. | |
| 5,480,804 A | 1/1996 | Niwa et al. | |
| 5,539,521 A * | 7/1996 | Otokake et al. | ............ 356/601 |
| 5,574,594 A | 11/1996 | Fowler et al. | |
| 5,594,235 A | 1/1997 | Lee | |
| 5,861,985 A | 1/1999 | Ikoh | |
| 5,991,028 A | 11/1999 | Cabib et al. | |
| 6,005,964 A | 12/1999 | Reid et al. | |
| 6,049,421 A | 4/2000 | Raz et al. | |
| 6,128,129 A | 10/2000 | Yoneyama | |
| 6,130,745 A | 10/2000 | Manian et al. | |

(Continued)

OTHER PUBLICATIONS

Arrasate M., et al., entitled "Prospective Analysis of Huntingtin Conformation and Degeneration in Neurons," Gladstone Inst Neurological Diseases, Departments of Neurology and Physiology, University of California, San Francisco, CA USA, p. 26 Aug. 5, 2002.

(Continued)

*Primary Examiner*—Jingge Wu
*Assistant Examiner*—Seyed Azarian
(74) *Attorney, Agent, or Firm*—Carol L. Francis; Douglas C. Limbach; Bozicevic, Field & Francis LLP

(57) ABSTRACT

The invention comprises a robotic microscope system and methods that allow high through-put analysis biological materials, particularly living cells, and allows precise return to and re-imaging of the same field (e.g., the same cell) that has been imaged earlier. This capability enables experiments and testing hypotheses that deal with causality over time intervals which are not possible with conventional microscopy methods.

38 Claims, 15 Drawing Sheets

U.S. PATENT DOCUMENTS

| | | | |
|---|---|---|---|
| 6,150,173 | A | 11/2000 | Schubert |
| 6,151,161 | A | 11/2000 | Mayer et al. |
| 6,160,662 | A * | 12/2000 | Uchida et al. ............... 359/390 |
| 6,175,642 | B1 | 1/2001 | Gobbi et al. |
| 6,204,962 | B1 | 3/2001 | Kawamura |
| 6,226,392 | B1 | 5/2001 | Bacus et al. |
| 6,246,785 | B1 | 6/2001 | Molnar et al. |
| 6,285,498 | B1 | 9/2001 | Mayer |
| 6,319,668 | B1 * | 11/2001 | Nova et al. .................... 435/6 |
| 6,483,948 | B1 | 11/2002 | Spink et al. |
| 6,517,781 | B1 * | 2/2003 | Coassin et al. ............. 422/102 |
| 6,818,403 | B1 * | 11/2004 | Kirk et al. ..................... 435/6 |
| 6,986,993 | B1 * | 1/2006 | Ghosh et al. ................ 435/7.1 |

OTHER PUBLICATIONS

Bahlmann K., et al., entitled "4Pi-confocal Microscopy of Live Cells," Ultamircoscopy, 87 (2001) 155-164.

Bradley J, et al., entitled "An Evaluation of Specificity In Activity-Department Gene Expression in Neurons," Progress in Neurobiology 67 (2002) 467-477.

Finkbeiner R., entitled "Robotic Microscope Monitors Gradual Cell Changes," Jul./Aug. 2002, Biophotonics International, p. 15.

Finkbeiner R., entitled "New Roles for Introns: Sites of Combinatorial Regulation of $Ca^{2+}$-and Cyclic AMP-Dependent Gene Transcription," Science's stke www.stke.org/cgi/content/full/OC_sigtrans;2001/94/pel pp. 1-4.

Finkbeiner R., entitled "Calcium Regulation of the Brain-Derived Neurotrophic Facto Gene," CMLS, Cell. Mod. Life Sci. 57 (2000) 394-401.

Finkbeiner R., entitled "CREB Couples Neurotrophin Signals to Survival Messages," Neuron, vol. 25, Jan. 11-14, 2000, Copyright © 2000 by Cell Press, pp. 11-14.

Friedman R., entitled "Is Neurodogeneration a Misnomer?" BioMedNet News and Comments, http://news/story?day=011115&story=2 pp. 1-2.

Guy R, et al., entitled "A Fluorescence Microscopy Based Genetic Screen to Identify Mutants Altered for Interactions with Host Cells," J Microbiol Methods Oct. 2000;42(2):129-38.

Humbert S., et al, entitled "The IGF-1/Akt Pathway is Neuroprotective in Huntington's Disease and Involves Huntingtin Phosphorylation By Akt," Dev Cell Jun. 2002;2(6):831-7.

Kam Z., et al, entitled "Probing Molecular Processes in Live Cells by Quantitative Multidimensional Microscopy," Trends Cell Biol Aug. 2001;11(8):329-34.

Medlin J., entitled "New Microscope Gives Scientists The Inside Scoop on Living Cells," Environmental Health Perspectives vol. 107, No. 11, Nov. 1999.

Reynaud K, et al., entitled "Confocal Microscopy: Principles and Applications to the Field of Reproductive Biology," Folia Histochem Cytobiol 2001;39(2):75-85.

Saudou F, et al., entitled "Huntingtin Acts in the Nucleus to Induce Apoptosis But Death Does Not Correlate With The Formation of Intranuclear Inclusions," Cell Oct. 2,1998;95(1):55-66.

Ward GE, et al., entitled "96-Well Plates Providing High Optical Resolution for High-Throughput, Immunofluorescence-Based Screening of Monoclonal Antibodies Against Toxoplasma Gondii," J Immunol Methods Nov. 19, 1999;230(1-2):11-8.

Ziauddin et al., entitled "Microarrays of Cells Expressing Defined cDNAs," Nature, vol. 411, May 3, 2001, www.nature.com.

* cited by examiner

ROBOTIC MICROSCOPY SYSTEMS

CROSS-REFERENCE TO RELATED APPLICATIONS

Benefit to U.S. Provisional Patent Application 60/337,585, filed Dec. 5, 2001 and entitled "Robotic Microscopy System and Method" is claimed. The entirety of that application (including its written Specification and the attached Drawings which provide additional information about the systems and methods of the invention) are hereby incorporated by reference, even such portions as not presently set forth herein.

BACKGROUND OF THE INVENTION

Inverted microscope configurations and computer control for automatic focusing and microscope stage positioning have been used for imaging of biological samples, for example, U.S. Pat. No. 4,000,417 discloses a computer automated system for blood cell counts and blood cell morphology studies. The system provides automated x-y stage translation, auto-focusing, and an automated meander search pattern system for cell finding. The system also provides for memorization of x-y positions for re-insertion of slides and re-viewing of previously viewed cells on previously used slides. U.S. Pat. No. 6,005,964 discloses an automatic microscope slide inspection system with a controllable stage positioner for scanning slides for pathogenic protozoa. U.S. Pat. Nos. 4,705,949 and 4,974,952 disclose cell chambers or holders microscopy of living cell specimens. U.S. Pat. No. 4,920,053 discloses a method for micromanipulation of living cells using an inverted microscope, and U.S. Pat. No. 5,991,028 discloses an automated spectral imaging system for cell classification. Ultramicroscopy 2001, April; 87(3): 155–64 discloses a method of two-photon 4Pi confocal fluorescence microscopy for imaging of live cells. Environmental Health Perspective 1999, November; 107(11) discloses a technique for imaging of living cells using an integrated optical magnetic resonance microscope. Folia Histochem Cytobiol 2001;39(2):75–85 discloses the use of confocal microscopy for fluorescently labeled thick specimens of stained living cells without requiring physical sectioning of samples.

Additional patents of interest include U.S. Pat. Nos. 4,920,053, 5,991,028, 4,705,949, 5,594,235, 6,005,964, 5,861,985, 4,000,417, 6,049,421, 6,246,785 and 4,958,920, the disclosures of which are incorporated herein by reference. Publications of interest include Anal Biochem Jun. 15, 2001;293(2):258–63, Ultramicroscopy 2001, April;87(3): 155–64, Folia Histochem Cytobiol 2001;39(2):75–85, Trends Cell Biol 2001 August;11(8): 329–34, J Microbiol Methods 2000 October;42(2):129–38, J Immunol Methods Nov. 19, 1999;230(1–2): 11–8, and Environmental Health Perspective 1999, November; 107(11); and Nature 2001 May; 411: 107–110. the disclosures of which are incorporated herein by reference.

Still, no available microscopy systems effectively provide for high throughput techniques for observation of living cells, with imaging of living cells carried out in a multi-well format. Particularly, no microscopy systems allow rapid imaging of living cells in a multi-well format without harm to the living cells, or allow quick and easy re-imaging of previously viewed living cells. The present invention satisfies these needs, as well as others, and overcomes deficiencies found in the background references.

SUMMARY OF THE INVENTION

The invention comprises a robotic microscope system and methods that allow high through-put analysis biological materials, particularly living cells, and allows precise return to and re-imaging of the same field (e.g., the same cell) that has been imaged earlier. This capability enables experiments and testing hypotheses that deal with causality over time intervals which are not possible with conventional microscopy methods.

The methods of the invention comprise, in one embodiment, providing an array comprising a plurality samples (e.g., a multi-well plate having a plurality of wells containing samples), and an optically detectable reference mark thereon, positioning the array in association with an objective of an inverted microscope, determining a location for each of the plurality of samples with respect to the reference mark, and storing location information for the wells in a computer memory. The objective may include a depth-of-field such that images of cells within the wells remain in visible focus over a plurality of depth positions. In an embodiment of particular interest, the array is a multi-well plate having a plurality of wells, wherein the wells contain one or more cells for analysis.

System hardware is configured to allow imaging on a substrate, (e.g., live cells grown on tissue culture plastic or other surface provided by a well) over extended periods of time (e.g., days to months) over which time the material may be observed periodically (e.g., hourly, daily, every other day, weekly, etc.) or otherwise as desired. In an embodiment of particular interest, the invention provides for imaging at the single cell level, particularly living cells, which cells may be dispersed on a substrate surface as isolated single cells or contacting other cells (e.g., as in a monolayer). Preferably, the biological material is immobilized or substantially immobilized, (e.g., as in when cells adhere to a substrate, such as tissue culture plastic (e.g., in a well)), so that the positions of the material being imaged are relatively fixed with respect to the substrate, permitting subsequent return to precisely the same field of objects (e.g., cells), even to the same object (e.g., individual cell) within a field. The invention allows for imaging of homogenous or mixed populations of materisl (e.g., the cells imaged can be a homogenous or heterogenous cell culture (e.g., a mixed cell culture)). Exemplary biological materials that are amenable to imaging according to the invention include, for example, nucleic acid (e.g., DNA, RNA, etc.), proteins, etc.

The invention optionally provides numerous features and advantages that include, inter alia:

the use of low numerical aperture objectives for imaging of cell collections (or other biological material) to provide a large depth-of-field such that that an image (e.g., of cells in a well) remains in visible focus over a wider range of Z-positions, thus requiring focusing only once per region (e.g., a well) or less often for high throughput imaging (e.g., focusing less than 20, 15, 10, 5, 3, or two times per multi-well plate; alternatively, spending about $\frac{2}{3}$, $\frac{1}{2}$, $\frac{1}{4}$, $\frac{1}{8}$ or $\frac{1}{16}$ the amount of time or number of times focusing as might otherwise be involved);

the use of autofocus to account for tilt of the substrate, especially, where relatively higher numerical aperture objectives are employed;

the use of a reference point on a multi-well plate and programming for stage movement for a multi-well plate such that the same cells in a well can be located and imaged at future time points the use of matrix registration, especially, in connection with reference point use in relocating an image field of interest or objects therein such as cells therin;

programming configured to automatically acquire non-overlapping images in a preset pattern for each well in a multi-well format; and the use of automatic switching between different fluorescence excitation and emission filter combinations via computer controlled positioning of dual filter wheels to resolve different structures or functional processes using multiple fluorescence indicators;

the use of focus compensation for different wavelength signals received in viewing different flours, especially in connection with higher numerical aperture objectives and the automatic fluorescence detection noted; and/or the use of a routine for qualifying image data by determining a minimum brightness or threshold value for a given set of circumstances in order to count the data as relevant for further analysis.

The automation of microscopy not only makes imaging faster, it makes it better. Automated image acquisition helps to overcome at least two problems associated with live cell imaging—photobleaching and phototoxicity. Both factors are directly related to the intensity and duration of illumination and the strategy that was adopted significantly reduced both. Manual focusing before image collection can contribute to toxicity and photobleaching because manual focusing often uses intense fluorescence illumination and the process can be lengthy. Limiting phototoxicity and photobleaching makes it possible to observe low intensity fluors (fluorophores) and to collect more images without perturbing cell/neuronal health than would otherwise be possible. Indeed, there are some fluorophores whose signals are so low or that photobleach so quickly that even the time that it takes to focus the instrument can lead to such significant bleaching that they lose much of their usefulness. With an approach of the present invention, using brief pulses of transmitted light to focus, and then capturing one brief fluorescence image, the illumination is minimized.

Several additional features besides those incorporated into the design of the imaging system may also be employed to enhance automated image analysis. For example, a high signal-to-noise ratio is useful. Particularly, in observing certain cells, particularly living cells, using a transfection marker reduces the potential for non-specific signals since a neuron must be transfected (and remain living) to generate significant fluorescence. By virtually eliminating background signals, a variety of fluorescent proteins can be used alone or in combination (e.g., CFP, YFP, GFP, and RFP), even if the proteins themselves differed significantly in the intensity of the fluorescence that they produce. Second, (particularly where neuronal observation is the goal) constructs may be used to produce high expression of the marker gene with relatively little variability from neuron to neuron compared with other constructs. Third, using a low transfection efficiency marker gene can be helpful. Low transfection efficiency can enhance visualizing and distinguishing each transfected cell apart from its neighbors. The ability to, for example, unambiguously distinguish one neuron and its processes from another can be important for single-cell and threshold-based automated analysis.

Of course, the present invention is not limited for the study of neurons. Such activity merely provides one example of its application. The present invention may be applicable in other settings as noted herein as well as others not specifically referred to. Though no further discussion follows, it is to be appreciated that many aspects of the present invention may be used in laser-capture microdisection applications, as part of a larger or more complex analysis system, and/or in other optical imaging/scanner systems (such as for scanning biopolymer arrays)—to name a few alternate applications.

Any of these and other objects, advantages, and/or features of the invention will become apparent to those persons skilled in the art upon reading the details of the invention as more fully described below. Still, it is to be understood that no variation or embodiment of the invention need present all such aspects. Certain variations of the invention will offer more features than others, while some may only offer or address any one of the noted considerations.

BRIEF DESCRIPTION OF THE DRAWINGS

Certain of the figures diagrammatically illustrate aspects of the invention; others are representative of the same.

DEFINITIONS

Figure 1:
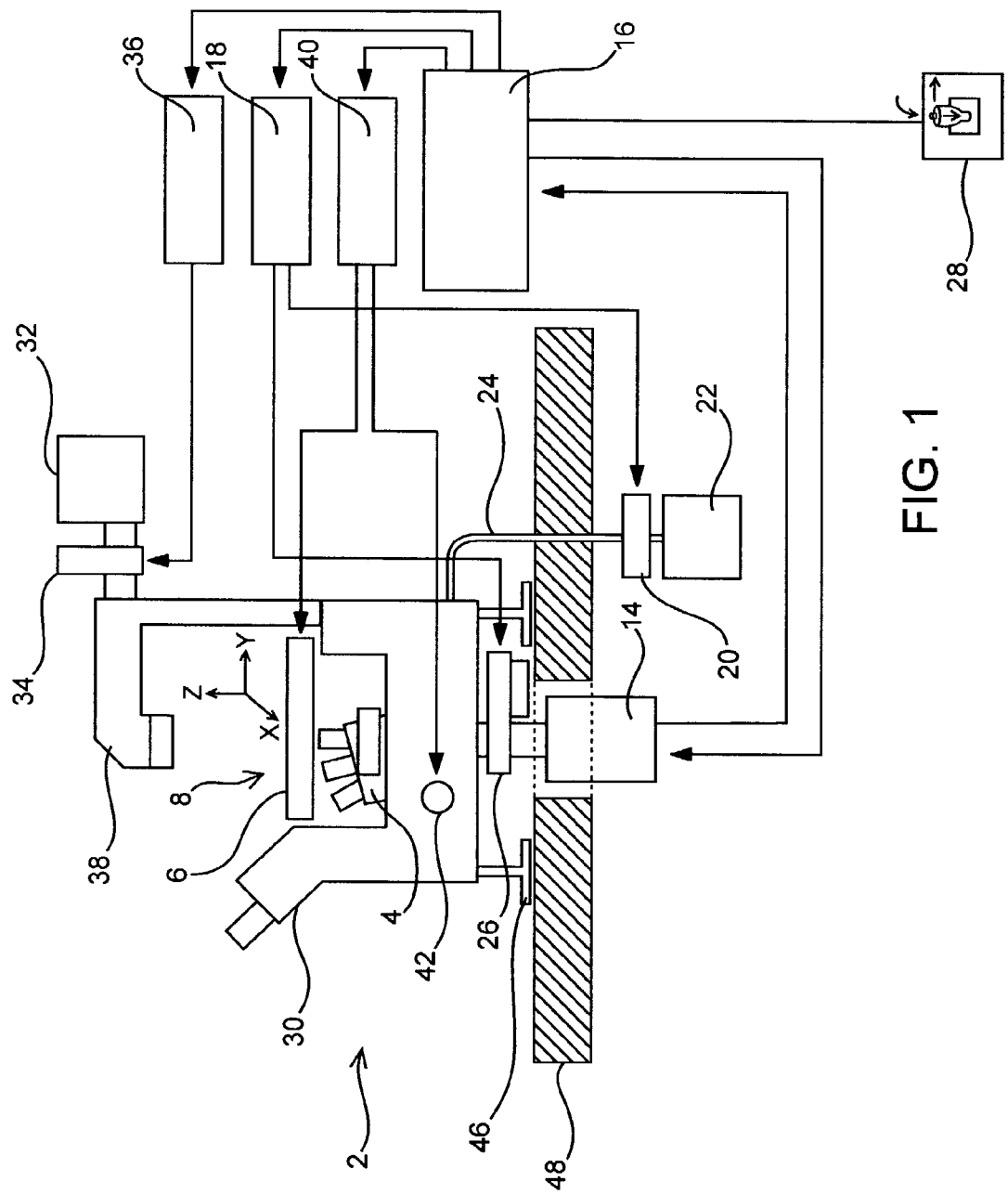
FIG. 1 schematically illustrates an optical scanner or microscope as may be used in the present invention.

Unless defined otherwise, all technical and scientific terms used herein have the same meaning as commonly understood by one of ordinary skill in the art to which this invention belongs. Still, certain elements are defined below for the sake of clarity and ease of reference.

In general, the systems and methods of the invention involve imaging of cells which are provided on a substrate. In this context, "substrate" is meant to describe the material on which the cells for imaging are provided (e.g., grown). The substrate may comprise a plurality of wells (i.e., at least two), which can be provided in an array format. A "multi-well plate" is a non-limiting example of such a well-containing substrate in which multiple discrete regions are provided, whereby the wells are provided in an array. Another manner of providing discrete regions is presented, for example, in Nature vol. 411: 107–110 noted above where a monolayer of cells is grown over DNA spots, whereby discrete image/analysis areas are provided. A further example is in a DNA or protein array. Substrates can comprise any suitable material, such as plastic, glass, and the like. Plastic is conventionally used for maintenance and/or growth of cells in vitro, and is referred to in the specification as exemplary of substrate materials without limitation.

By "well" it is meant generally a bounded area of a substrate (e.g., defined by a substrate), which may be either discrete (e.g., to provide for an isolated sample) or in communication with one or more other bounded areas (e.g., to provide for fluid communication between one or more samples in a well). For example, cells grown on the substrate are normally contained within a well, which can further provide for containing culture medium for living cells.

A "multi-well plate", as noted above, is an example of a substrate comprising wells in an array. Multi-well plates that are useful in the invention can be of any of a variety of standard formats (e.g., plates having 2, 4, 6, 24, or 96, wells), but can also be in a non-standard format (e.g., 3, 5, 7, etc. wells).

By "discrete region" it is meant a spot or grouping of interest that may be bounded (as in a well) or simply have a definable boundary, separate from other adjacent units. Whether presented in an array or otherwise, such discrete regions are advantageously provided in a preset pattern. Oftentimes, the pattern will be regular and repeating, though it need not be.

DETAILED DESCRIPTION OF THE INVENTION

Before the subject invention is described further, it should be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting.

For example, reference to a "well" or a "multi-well plate" is made throughout the specification for the purposes of clarity and convenience only, and is not meant to be limiting as to the substrate, since aspects of the present invention encompass imaging of any discrete region as described herein or otherwise. It should also be apparent from the context herein, that many aspects of the invention are applicable to imaging or scanning any region—whether discrete or not. Furthermore, while the invention is described primarily in terms of use with biological samples and living cells, it may, however, be used for imaging of any types of samples, with biological materials being or particular interest. For example, the invention can be used in imaging and analysis of a variety of biological materials, such as cells, particularly living cells; the specification refers to "cells" throughout for the purposes of clarity and convenience only, and is not meant to be limiting. In addition, the invention can be applied to acquisition and analysis of any suitable optical image, of a variety of different spectral ranges, e.g., any range of color, produced for example by, reflected light fluorescent emissions, luminescent emissions, chemiluminescent emissions, etc. Reference is made throughout the specification to, for example, phase contrast and fluorescent images, however the invention is not so limited. The scope of the present invention will be established by the appended claims.

As used herein and in the appended claims, the singular forms "a", "and", and "the" include plural referents unless the context clearly dictates otherwise. Thus, for example, reference to "an image" includes a plurality of such images, and reference to "the objective" includes reference to one or more objectives and equivalents thereof known to those skilled in the art, and so forth. It is further noted that the claims may be drafted to exclude any element indicated herein to be optional, especially by use of permissive language. Accordingly, this statement is intended to serve as antecedent basis for use of such exclusive terminology as "solely," "only" and the like in connection with the recitation of claim elements, or use of a "negative" limitation.

The publications (including patents) discussed herein are provided solely for their disclosure prior to the filing date of the present application. Nothing is to be construed as an admission that the present invention is not entitled to antedate such publications by virtue of prior invention. All publications (again, including patents) mentioned herein are incorporated herein by reference to disclose and describe the methods, systems or other subject matter in connection with which the publications are cited.

As to the invention, it features an automated or robotic microscope system and methods that allows high throughput biological analyses on living or fixed cells. One aspect of the invention allows for precise return to and re-imaging of the same field of living cells that have been imaged earlier. This capability enables experiments and test hypotheses that deal with causality over time intervals which are not possible with conventional microscopy methods.

System hardware is preferably configured to allow imaging of live cells grown on tissue culture plastic that can be maintained for long lengths of time (days to months) in tissue culture dishes. By growing cells on a substrate (e.g., tissue culture plastic), cell positions become relatively fixed with respect to the substrate, which permits subsequent return to precisely the same field of cells.

The invention is implemented by way of hardware, optionally as described below, and computer programming. Programming embodying the features or methodology described herein may be originally loaded into the automated microscope, or the microscope may be preprogrammed to run the same. Such programming, routines and associated hardware constitute various "means" as may be referenced in the claims made hereto. For example, the programmed computer referenced herein comprises a means for directing the action of the various controllers provided. Associated programming can be recorded on computer readable media (i.e., any medium that can be read and accessed by a computer). Such media include, but are not limited to: magnetic storage media, such as floppy discs, hard disc storage medium, and magnetic tape; optical storage media such as CD-ROMs and DVDs; electrical storage media such as RAM, ROM and EPROM; and hybrids of these categories such as magnetic/optical storage media.

Various aspects of the system and methods of the invention will now be described in more detail. Such description are followed by Examples providing additional, optional aspects of the invention.

Figure 2:
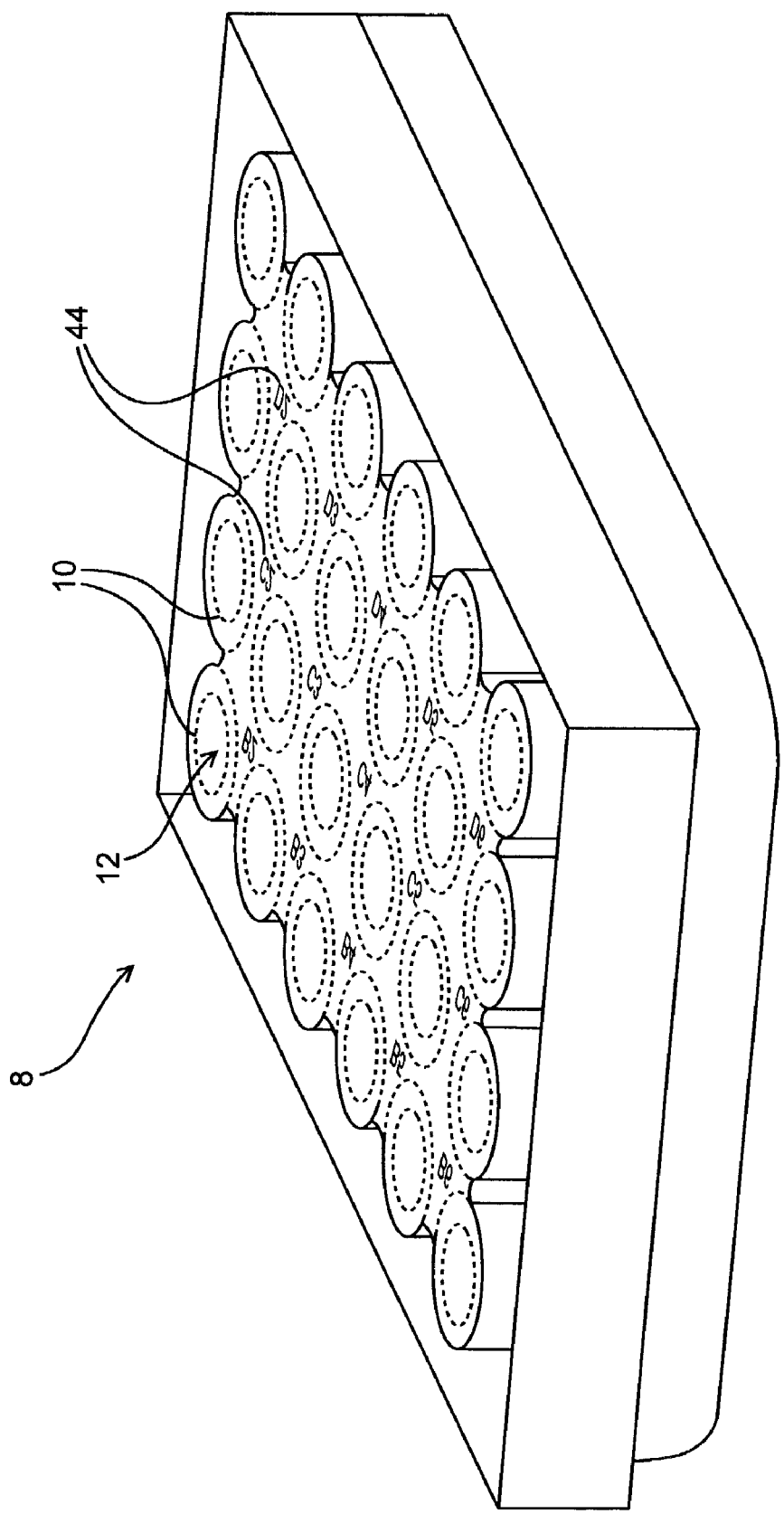
FIG. 2 is a perspective view of the underside of a multi-well plate as may be used in growing, storing and observing cells with the automated microscope of FIG. 1. The side shown is that which faces to the optics of an inverted microscope for inspection, though the plate itself will generally be right side up in use.

Optical layout and acquisition hardware. In view of the above considerations as shown in FIG. 1, an inverted microscope body 2, with objectives 4 positioned beneath the stage 6, is used to image living neurons in standard tissue culture dishes and to keep the specimen plane a relatively fixed distance from the objectives. The fixed distance makes automated image acquisition faster and more accurate. FIG. 2 shows a dish or well plate 8 with individual wells 10 for samples. Imaging is generally performed through the base material 12 of the culture dish or well plate as will be discussed further below in terms of reducing phototoxicity. The camera 14 (e.g., comprising a CCD (charged coupled device)) is shown placed directly beneath the microscope body to eliminate the need for an extra mirror within the microscope body that could reduce the amount of emitted light. A fast, high sensitivity 14-bit CCD camera with a wide dynamic range is used for high throughput capability with computer control, to allow resolving and measuring of objects based on intensity, and so that less illumination of the specimen is required. Programmed computer 16 controls automatic switching (via controller 18) between different fluorescence excitation and emission filter combinations is achieved by interposing one position filter wheel 10 (Sutter Instruments) or filter wheel and shutter combination 20 between a Xenon light source 22 and a fiber optic (liquid light guide) 24 that carries the light to the microscope (excitation) and another filter wheel 26 between the microscope body and the camera (emission). Automated filter changes (again, via controller 18) make it possible to resolve and relate different structures or functional processes using multiple fluorescence indicators.

Additional hardware may include a manual input/control device 28 such as a "joy-stick" in order to manually scan the plate to verify features though eyepiece(s) 30. Though such features are not required of the present invention, they provide a convenience to which many users are accustomed. Also, vibration isolating footings 46 to interface with a table 48 or other support surface may be advantageously employed.

Additional desirable hardware is presented for use in connection with system focusing. Such hardware includes an incandescent light source 32 moderated by an electronic shutter 34, which is in turn operated by a controller 36. When the shutter is open, light is transmitted from the source via optics 38 to illuminate the field of view of the objectives. Such lighting is utilized, preferably in connection with phase contrast optics where a plastic well plate is used, to enable focusing without the use of the xenon light source.

Such an approach using a secondary light source is desirable in that very low intensity (substantially) white light is all that is required to achieve focus. It also avoids dependence on light from fluorescent objects that may become less numerous or even dissapear over time. In contrast, with use of the xenon light source and utilizing fluorescence resultant upon exposure of a sample to the same requires much greater light intensity that can and will result in sample phototoxicity. The focus routines discussed below further limit the potential effects of phototoxicity (even by virtue of exposure to light source 32) by minimizing time spent under illumination for the purpose of focusing.

Microscope Objectives. A Nikon body, such as in a model TE300 unit, can be used to take advantage of the extra long working distance lenses provided by longer tube length for the objective. This makes it possible to capture a focal plane that is farther (many millimeters) away from the tip of the objective but still have a relatively good numerical aperture. The relatively long working distances offered by the setup allows focusing beyond the floor of the tissue culture plate 8, into thick specimens such as transfected neurons within a brain slice without bumping the objective into the dish. Generally, such samples range in thickness from about 50 to about 400 microns. The 4× objective from Olympus Uplan SL 4×\0.3\ PhL may also be used, which transmits roughly the same amount of light as the Nikon objective. However, the Olympus objective transmits light more evenly across the field, and the difference in transmission from the edge of the field to the center of the field is twice as good for the Olympus objective than for the Nikon objective.

A 4× image is especially well suited for counting cells (e.g., measuring survival) and for some measurements of overall morphology. Normally, a relatively high numerical aperture objective is preferred to allow collection of more light (i.e., form an image with less signal) with better spatial resolution. In the microscope system of the invention, however, a relatively low numerical aperture lens can still collect enough light to form an image while providing substantially greater depth-of-field such that that the image remains in visible focus over a wider range of actual Z-positions. This allows focusing once per well (preferably, in the center) followed by capture of a series (e.g., 3×3 or 4×4) of adjacent fields within the same well, that remain in focus. Focusing only once per well cuts the time required to image or scan a 24-well plate by one half.

Automated focusing. Commercial imaging software from Metamorph (Universal Imaging Corporation (UIC)) or customized software provides software drivers that are able to automatically focus the microscope via stage controller 40. The drivers send signals to motors that control an X-Y stage position and a Z-axis focus knob 42. Stepper motors may be employed to automate such movement (not shown). Generally, to focus an image that is collected by the system optics, a fast-Fourier analysis is performed to measure the spatial frequency of the image, and then the computer moves the Z-position and repeats the analysis at a new depth. A local maxima in spatial frequency is determined which corresponds to the focal plane. As referenced above, transmitted light (rather than epifluorescent images) is preferably used for focusing because reduced light exposure intervals are required (which limits phototoxicity) and fast acquisition times. The CCD camera resolution can be reduced during image acquisition for determination of the focal plane to increase speed. This provides up to a 100-fold improvement in acquisition speed and substantial reduction in phototoxicity.

Efficient focus routines. A first routine or process as introduced above may be utilized in connection with low numerical aperture optics to avoid significant time expenditure associated with purely adaptive focus routines as noted further below. A second routine or process is utilized with objective having intermediate to high numerical apertures (e.g., 10×, N.A. 0.30; 20×, N.A. 0.45; 40×, N.A. 0.60) dept of field decreases relative to the previous exemplary optics.

In this first process, using a generally low magnification, generally low numerical aperture "N.A." objective (e.g., 4×, N.A. 0.13) the system is focused a single time for each well to be examined utilizing that single focal setting in acquiring images from the entire well. In some instances, however, it may be appropriate to focus only a single time per plate (imagening each inidividual well at the same focal setting). In such cases, it may be desired to focus at the center well or a near-center well in the substrate/plate in order to approximate an average position relative to other wells that may be located higher or lower.

In practice, it should be noted that the acceptable limits of aperture and/or magnification affecting depth of field will vary in accordance with the sample to be examined. Neurons, for instance, may require a greater depth of field to examine due to the manner in which they tend to interweave as they grow in such a way that they may occupy several planes. What is required according to the present methodology is that a discrete sample area (such as a well 12) is examined automatically to gather adjacent images with a focus set either by a single examination for focus purposes of that area or alternatively by a focus setting determined for an adjacent, near-by or associated area.

Figure 6A:
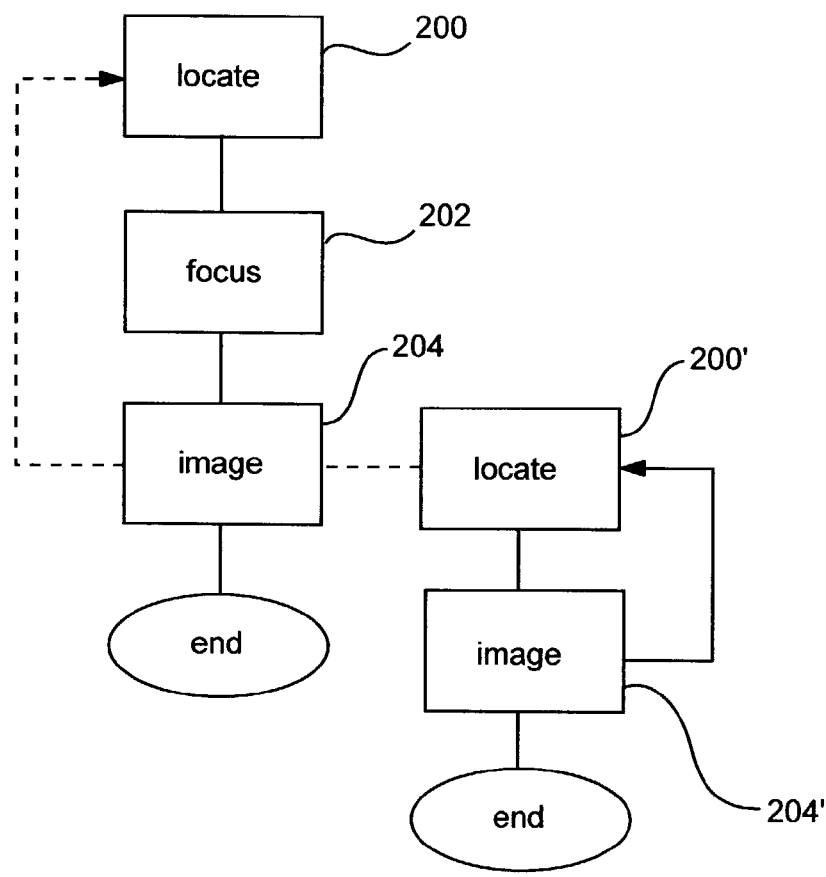
FIG. 6A is a flowchart representing a first focus routine simplification process.

In any case, such methodology is presented in FIG. 6A. Here, two imaging approaches are shown. Each generally begins by a well location step or act 200. Where focus is to be made only once, the well is preferably located at the center of a multi-well plate. Otherwise, any well will suffice.

Once located along X and Y coordinates, a focus step 202 occurs to determine Z-axis positioning of the various system 2 elements involved. Generally, focus will occur in the center of a well (to account for averages—such as introduced by substrate tilt—and/or to avoid meniscus effects). Next, that well or another well (where a single focus approach is employed) is examined in step 204.

Where focus is desired for each well, the optional dashed route to the left returns the process to step 200. The above process is repeated until imagening is complete. In instances where a single-focus approach is desired the other optional dashed route to the right is followed to a subsequent well location step 200'. Well imaging 204' follows, with location and imaging acts repeated until imaging is complete.

For objectives with intermediate to high magnification and/or numerical apertures (e.g., 10×, N.A. 0.30; 20×, N.A. 0.45; 40×, N.A. 0.60) depth of field decreases relative to the previous exemplary optics. Accordingly, a single-focus and imaging approach is often not feasible. Yet, the invention contemplates a simplified focus maintenance scheme for such optics and in other situations where the depth of field offered is not adequate to feasibly collect data over a sufficiently large adjacent area or surface.

Namely, in such instances where well plate tilt or other variances are presented, focus can be made for each well (sometimes a single time for an entire well plate) and modified according to a measured slope of each well (or the overall plate/substrate). In a preferred approach, at least three focus measurements are taken in a given well at spaced-apart points. These at least three points define a plane having a tilt or slope that is calculated. Based on this slope, Z-axis movement is modified to maintain focus as would be predicted or expected as X and Y stage movement occurs.

Of course, this methodology may be implemented in a number of manners. As noted, the system may focus on the sample to be examined to determine the tilt plane. Alternately, it may focus on the surface of or features on the substrate or plate carrying the sample to define the relative position(s) of the same with respect to system optics and apply such data to focus calculations once determined for the sample to be observed.

Figure 6B:
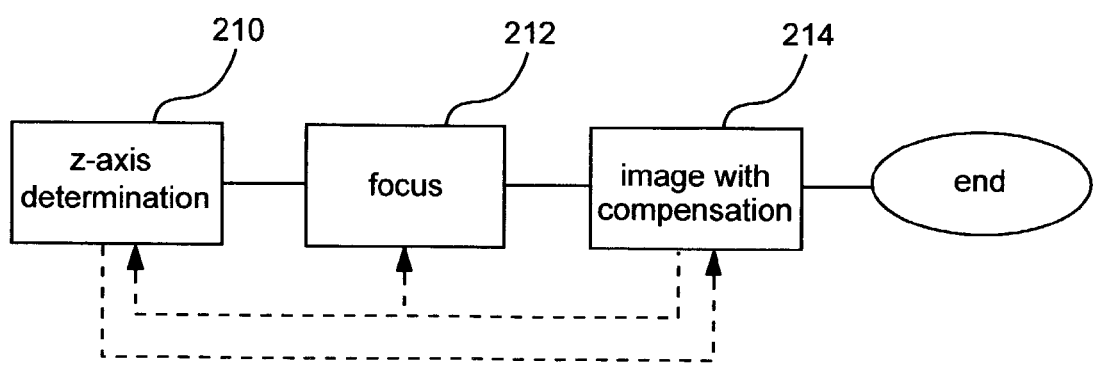
FIG. 6B is a flowchart representing a second focus routine simplification process.

Reference to FIG. 6B depicts the most basic process steps or acts involved in the second efficient-focus approach according to the present invention. Particularly, the process includes an act of Z-axis determination 210 in which at least three focal points that will provide a slope or tilt for the substrate are located. Sometimes, focus determination will be followed by a focus step 212 for a point in a given well of a substrate. Otherwise, the process will jump directly to imaging 214 one or more wells of the substrate (e.g., where focus information has already been obtained by virtue of the Z-axis determination). Imaging according to step 214 occurs so that focus position is modified according to the plane slope determination for the substrate or that of the cells in a well.

As stated previously (and as indicated by the dashed arrow returning from the imaging 214 to Z-axis determination or focus step 212) Z-axis determination (i.e., for slope calculation) and focusing may be done for each well or the entire well-plate. Where minimal depth of field is offered by the optics, a well-by-well approach will be called for. Where precise focus is less critical (even as an alternate approach to that in FIG. 6A) focus compensation according to the approach in FIG. 6B for the entire substrate may suffice.

Controlling automated stage movements. As referenced above, programming may be provided (e.g., using script language in connection with the Metamorph program and various software modules of Metamorph to automatically acquire non-overlapping images in a preset pattern from each well in a multi-well dish. The script moves the stage to the first well (or grid location/quadrant), changes the acquisition settings for transmitted light, automatically focuses the microscope, changes the settings for epifluorescence by moving the filter wheel to the correct position, acquires the image, and names and stores the file. In each well or across multiple wells (perhaps even all the wells), focus can be maintained as discussed above. The cycle is repeated for a preset number of adjacent non-overlapping fields within a single well before it moves to the next well, until the entire multi-well dish is complete.

The pattern may move from inside (from the center of the well) outward. Spiral, box-step or another fashion of movement may be employed. Starting in the center of the well is, however, preferred in that it allows for focusing (where an initial focus set is to be employed) at a point unaffected by meniscus effects closer to the sides of a well.

Figure 3:
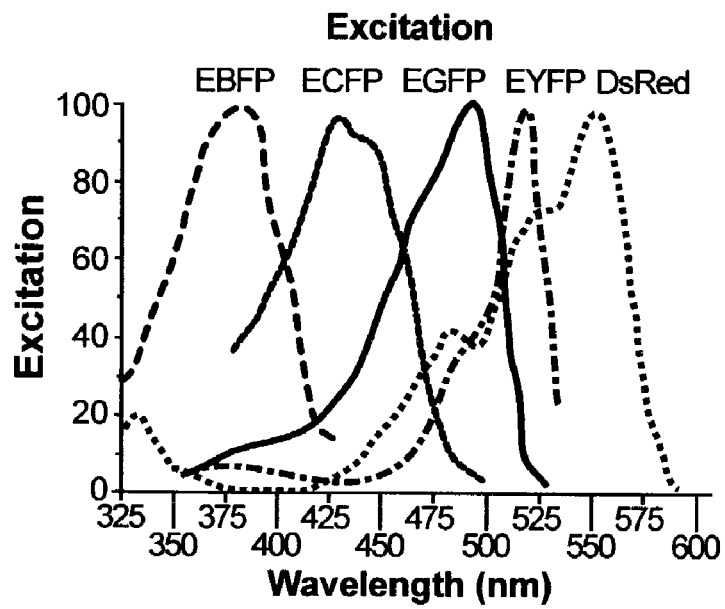
FIG. 3 is a graph showing various excitation emission spectra for various fluorophores.

Wavelength compensation. Another manner of improving focus efficiency is presented in connection with wavelength compensation. Especially in connection with higher numerical aperture objectives, the invention preferably automatically contemplates varying focus depending on the approximate wavelength of light received by the optics. Especially where the system automatically switches between epifluorescence settings by moving the filter wheel as noted above, automatically adjusting focus in concert with such change provides a dramatic benefit. In this regard, FIG. 3 shows the emissions of 5 common flurophores as may be used. The light emitted by each has a different peak wavelength. Even with color-corrected optics (due at least to the light passing through the base of plate 8) the wavelengths will be in sharpest focus at different points. Accordingly, in the invention focus settings are modified according to empirically tested differences based on which flour is examined.

Figure 7:
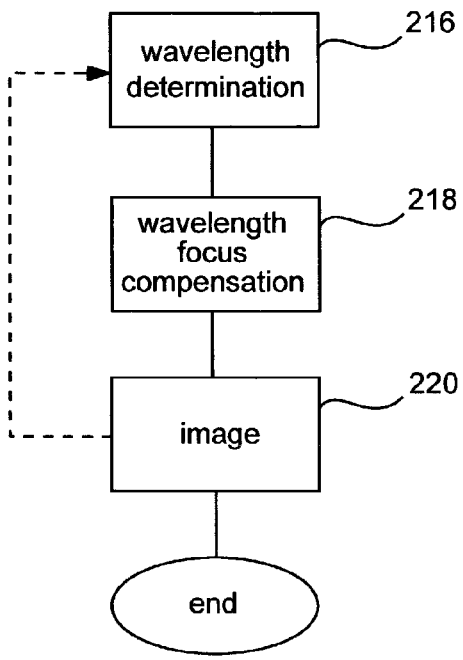
FIG. 7 is a flowchart representing automatic focus wavelength compensation.

Such activity preferably occurs in a fully automated manner, with computer 16 coordinating the activity of stage controller 40 and filterwheel controller 18. Still, other automated or semi-automated approaches are possible in the invention. The flow of any such process is generally indicated in FIG. 7. Based on the set or determination 216 of the wavelength emission to be detected in view of certain hardware settings, a focus compensation step 218 follows. The compensation step involves modifying the focal distance between the substrate and the microscope object/optics. Such action is followed by an imaging step 220.

Imaging step 220 may occur in connection with a single well. Especially in such instances, the process will often track along the dashed line to run through a number of fluorophores for each well. Alternately, every well can be imaged during step 220 using a single fluorophor and the process of determining wavelength and accounting for the same be performed for successive imaging or scans of every well detecting a different fluorophor.

Returning to the same field. The programming of the present invention allows imaging a field of cells and then subsequently returning to and re-imaging that same field of cells at any time interval. Such activity enables study of cause-and-effect relationships in living cells over days or weeks by returning to image the same cells. The invention may use one or more reference marks on a multi-well plate to quickly position the plate in the plate holder on the microscope stage each time the plate is returned to the microscope for imaging. The mark may be one that is consistently set on or into the well plate such as alphanumeric identifiers as element(s) 44 seen in FIG. 2. Alternatively, one or more custom-applied reference points, marks or structures may be employed.

The mark serves as an internal reference for cells on the plate, independent of the position of the plate within the holder. The user puts the plate in the holder and the stage is moved approximately to the mark and focused thereon. The user then manually moves the stage (e.g., with a joystick control 28) to get the mark in the exact same position as is shown in a previously captured reference image, and the acquisition programming is started with the mark in exactly the same position as the reference image (and therefore the same position each time the cells are re-imaged) so that each image in each well is also in the corresponding position.

Returning to a reference mark and finding a position in relation to that mark provides one manner of returning to the same field to observe stationary or substantially stationary cells at separate time intervals. Where more accurate return to a field is desired or required, further refinement of the process is in order. The invention is able to align images within at least several pixels, even with accuracy to a single pixel or in perfect registration utilizing supplemental mathematical techniques.

Figure 5:
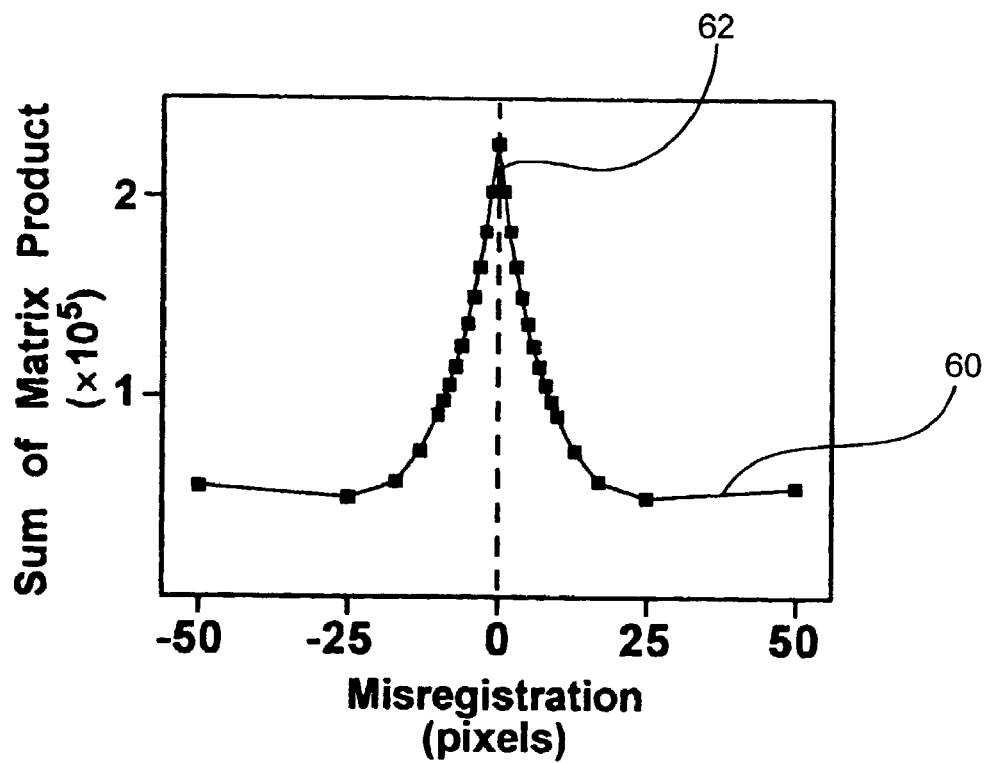
FIG. 5 is a graph illustrating a pixel registration approach according to the invention.

Particularly, in this aspect of the invention, image data obtained is digitally stored. This data is converted to a matrix of values. Signals below a threshold value are treated as zeros while others are treated as numerical values (e.g., ones for the sake of simplicity, in which case the matrix will have been binarized). Second or subsequent imaging of approximately the same region (preferably, as generally identified by use of the reference mark(s) as described above) receives the same treatment. By multiplying the matrices, registration information as presented in FIG. 5 is provided.

Since misalignment of images (as in survivability studies, etc.) to be superimposed via computer software for analysis, results in zeros multiplied against numerical values and greater mismatch of the matrices exacerbates this effect, lower sums 60 for the multiplied matrices represent less aligned positions. Conversely, a peak or spike 62 represents a maximum value of the sum of matrix numbers—indicating full (or at least optimized) alignment.

It may in some instances be preferred to utilize a subset (e.g., the central 80%) of the matrices in the registration process. Such an approach helps avoid situations where a portion of one matrix is not represented in the other matrix (and therefore would not contribute to the sum to identify a local maximum—unless the matrices were already identical/aligned) and the potential for unpredictability associated with the same. Furthermore, taking a subset of the available matrix values lowers computational requirements.

Note that even smaller matrices than the exemplary 80% approach may be employed —at least to roughly align images. By further reducing the computation demand on the system (by utilizing smaller matrix subsets), it becomes increasingly feasible to attempt registration of larger sampled areas. Also, with reduced computational demands, it will in some cases be possible to register images that are coarsely aligned (e.g., initially aligned without involving the reference mark approach).

Figure 8:
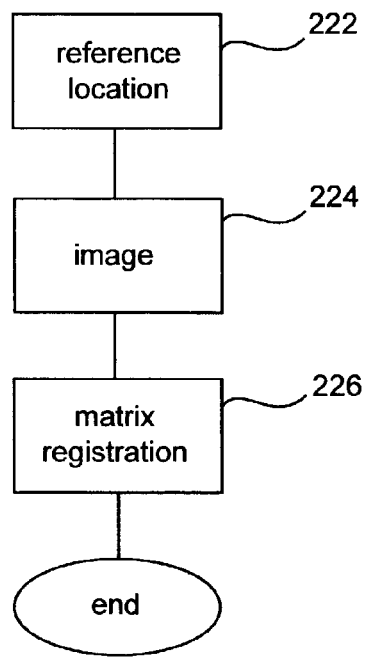
FIG. 8 is a flowchart representing certain aspects of aligning image data utilizing a registration matrix.

FIG. 8 provides a flow chart overview of the process as it is preferably run. By means of computer memory and associated control algorithms, direct user input or otherwise, a reference or fidelity point for the substrate employed is located in step 222. Such action is followed by an imaging step 224. Preferably, a phase contrast image is produced. However, fluoroscopic imaging of the cells may be employed. In any case, the image from step 224 is ultimately superimposed with a previous image that is likewise imaged in relation to the reference point. The superposition is preferably accomplished using a matrix registration technique 226 as described above in which the highest sum of the product of two matrices (or matrix subsets) representative of the pixel values is sought. In instances where the information utilized for registration is a phase contrast image, it should be paired for registration with another such image previously provided. The use of phase contrast images over flour-based images is preferred because little, if any, difference should be presented by the phase contrast images.

When registration is performed in connection with one image and subsequent imaging follows, these latter-produced images will be aligned or superimposed as well. While it may be preferred to conduct subsequent scans/imaging in such a manner and the computer processor directs stage movement (generally X and Y-axis movement) to align the images that no post computer processing is required to align them, an alternate approach is to perform registration of the images after all imaging is complete (i.e., off-line). That is to say, stored image data can be aligned using the matrix approach described. Usually, use of the a reference point or stored reference position will still be desired for rough alignment, to be followed with fine alignment performed with the matrix method. Accordingly, both on-line and off-line registration techniques are taught hereby.

In an exemplary implementation of this aspect of the invention, computer programming directs taking two pairs of images. It directs taking a first phase contrast image and first fluorescence image, then directs movement of the system's fluorescence emission filter wheel, followed by taking a second pair of phase and fluorescence images. Because movement of the filter wheel is often the cause of image misalignment in the referenced system, each pair of phase and fluorescence images (collected while the wheel is stationary) are aligned. However, the first and second image pairs are usually misaligned/misregistered with respect to the other, e.g., due to perturbation of the system caused by movement of the filter wheel. The misalignment is preferably corrected automatically via computer control employing the matrix methodology described above utilizing matrices derived from the more comparable phase contrast images that correspond to the fluorescent images—at least in terms of their registration.

Transfection method for cluster-free cell growth. In one embodiment, the invention takes advantage of a low efficiency transfection method for cultured cells (particularly neurons) that provides fluorescence images that are very well suited for automated image analysis. The method is a modification of the calcium phosphate transfection method for neurons and it typically leads to transfection efficiencies in the range of 1–5%. Although the rate is low, the high density culture leads to an overall high number of transfected neurons that tend to be evenly (randomly) distributed across a field with very few clusters, which is ideal for image analysis. Such an exemplary transfection method is provided by a http URL to "web1.ucsf.edu/labs/finkbeiner" under "Online Resources", then "Protocols" under the headings "Protocol for the Primary Culture of Cortical and Hippocampal Neurons", which describes preparation of a primary culture suitable for transfection, and "Calcium Phosphate Transfection of Neurons in Primary Culture".

Automated image analysis. Software may be provided, for example, custom software (e.g., as in script language) or using Metamorph as above to take each image in a directory, threshold it, subject the thresholded objects to an electronic filter to classify the objects as ones to be counted or measured, and then to make the counts or measurements, and store the information in a text file that can be later loaded into a spreadsheet or further manipulated or worked upon manually or electronically.

Also, custom thresholding software may be provided. This optional aspect of the system relies on an observation by the present inventor of a generally linear relationship between two basic factors determinable from raw image data stored in a file. Namely, by employing the minimum recorded pixel value and calculating the standard deviation of the mean calculated threshold value a line fit may be obtained that is approximately 5% more accurate in characterizing cell image data. Utilizing the equations, $$y=mx+b$$

$$b=v+k$$

where "x" is the standard deviation of the mean, "m" (the line slope), "b" is the y-intercept of the line equation, "v" is the minimum pixel value obtained in imaging, "k" a constant are empirically determined, a calculated threshold value "y" is produced. Images equal to brighter than the threshold value are qualified and subject to further analysis, optionally as described below. Pixel values lower than the threshold value are discarded in any analysis as irrelevant.

Once thresholding has occurred, adjacent pixels or groups of pixels may be classified for further purposes of analysis by a geometric filter. In such a filter, parameters that provide useful information in this regard (e.g., in running Metamorph and/or MatLab) include the following:

| | |
|---|---|
| Width | EFA2, Ellipse Area |
| Height | EFA2, Axial Ration |
| Length | EFA2 (Semi-Major Axis), |
| Breadth | (Semi-Minor Axis) |
| Fiber Length | Average of Semi-Major, |
| Fiber Breadth | Semi-Minor Axis |
| Perimeter | Average Gray Value |
| Centroid X | Total Gray Value |
| Centroid Y | Optical Density |
| Inner Radius | Integrated OD |
| Outer Radius | Intensity Center X |
| Mean Radius | Intensity Center Y |
| Equivalent Radius | Radial Dispersion |
| Total Area | Relative Hole Area |
| Pixel Area | Standard Area Count |
| Area | Texture Difference Moment |
| Orientation | Texture Inverse Difference Moment |
| Shape factor | OD Variance |
| Ell. Form Factor | OD Low Area |
| Equivalent Sphere Vol. | OD Medium Area |
| Equivalent Prolate Vol. | OD High Area |
| Equivalent Oblate Vol. | OD Low Amount |
| Equivalent Sphere Surface Area | OD Medium Amount |
| EFA 1.AO | OD High Amount |
| EFA 1.CO | OD Low Distance |
| EFA 2, Semi-Major Axis | OD Medium Distance |
| EFA 2, Semi-Minor Axis | OD High Distance |
| ERA 2, Semi-Major Axis Angle | Hole Area |

Figure 4:
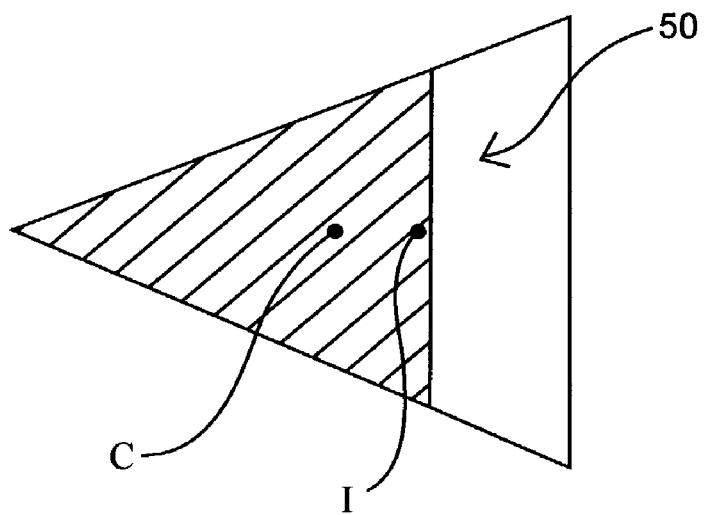
FIG. 4 represents a group of pixels in connection with characterization parameters.

FIG. 4 is demonstrative of such parameters that may be employed in characterization. Namely, an object formed by pixels 50 is characterized by its centroid "C" and intensity center "I". By combinations of these factors and those presented above, those with skill in the art may adequately categorize most, if not all, cell types as may be observed utilizing the system of the present invention.

Figure 9:
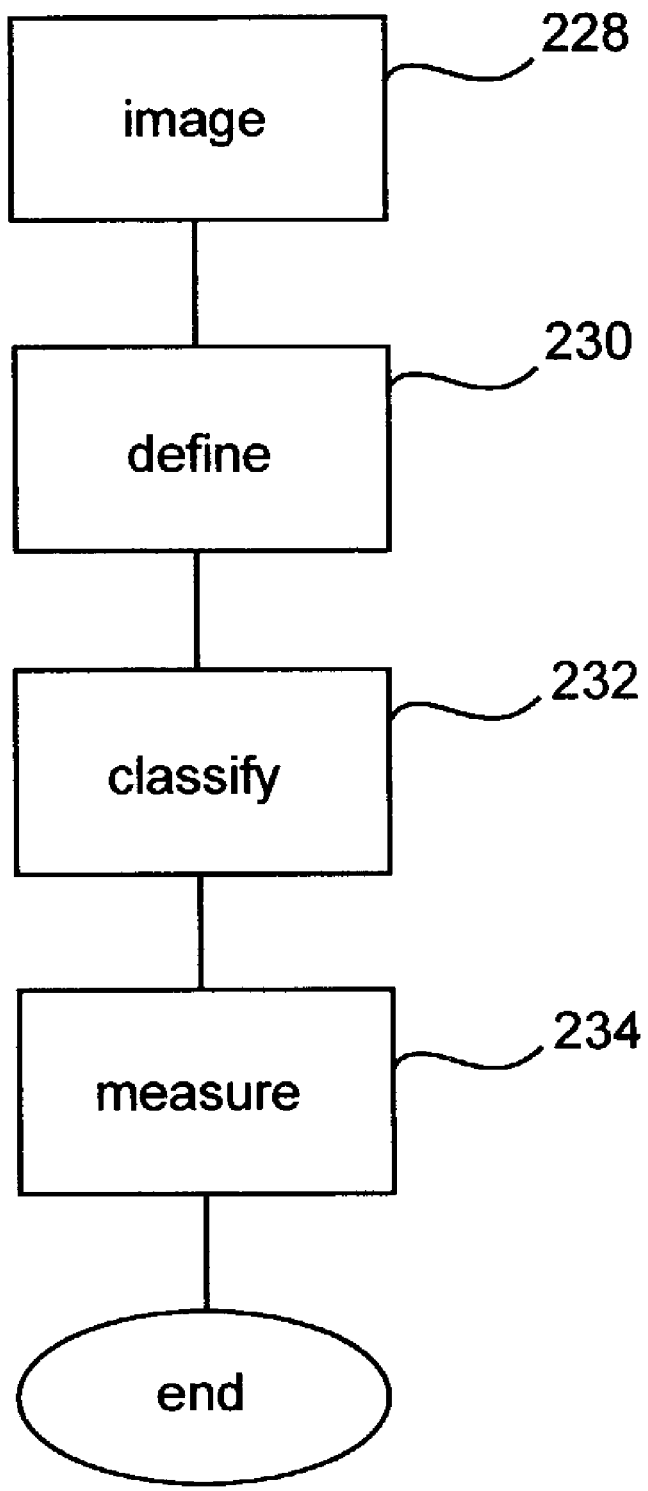
FIG. 9 is a flowchart representing an image data analysis procedure according to the present invention.

The categorized data, in a preferred example of the invention, may correspond to a live neuron count for purposes of measuring survival of one or more populations of cells. In any case, by categorizing the data, meaningful statistical analysis of one sort or another may be performed. FIG. 9 shows the manner in which such activity generally occurs. First data is obtained via one or more imaging steps 228. This data may be obtained in any manner as described above or otherwise. Upon obtaining the data, a definition step 230 is performed. In this portion of the process pixels meeting threshold values are retained as potentially relevant data. These image pixels are grouped with adjacent (preferably contiguous pixels) and thus defined as objects. Next, classification 232 of the objects proceeds in accordance with some combination of the various classification parameters noted above, or otherwise. Finally, data (e.g., regarding a particular cell variable, such as live vs. dead or such other applications noted herein) is obtained in a measurement step 234, which tallies and or records hard numbers relating to the classified information. The process can be repeated in its entirety or at any of the various stages to count additional variables (e.g., additional cell variables) or the like as may be detected with other markers.

In running the process, higher magnification levels will generally result in a lower object count; conversely, lower magnification levels will generally result in higher counts. Accordingly lower magnification settings may prove more efficient in some instances. Yet it will sometimes be required to use higher magnification in order to resolve smaller bodies or portions thereof to track biologic variables (e.g., cell variable).

Exemplary cells and samples for imaging analysis. The systems and methods of the invention can be readily adapted for imaging of any of a variety of cells, which may be provided in a variety of different formats in association with the substrate. For example, the cells can be a prokaryotic or eukaryotic cell, including bacteria, protozoa, fungi, and cells of avian, reptile, amphibian, plant, or mammalian (e.g., primate (e.g., human), rodent (e.g., mouse, rat), lagomorph, ungulate (e.g., bovine, ovine, swine, and the like), etc.) origin. Cells include primary cells, normal and transformed cell lines, genetically-modified cells and cultured cells. The American Type Culture Collection (Manassas, Va.) has collected and makes available over 4,000 cell lines from over 150 different species, over 950 cancer cell lines including 700 human cancer cell lines. The National Cancer Institute has compiled clinical, biochemical and molecular data from a large panel of human tumor cell lines, these are available from ATCC or the NCI (Phelps et al. (1996) *Journal of Cellular Biochemistry* Supplement 2:32–91). Included are different cell lines derived spontaneously, or selected for desired growth or response characteristics from an individual cell line; and may include multiple cell lines derived from a similar tumor type but from distinct patients or sites. Culture of cells is typically performed in a sterile environment, for example, at 37° C. in an incubator containing a humidified 92–95% air/5–8% $CO_2$ atmosphere. Cell culture may be carried out in nutrient mixtures containing undefined biological fluids such as fetal calf serum, or media which is fully defined and serum free.

Of particular interest is imaging of neuronal cells and neuronal precursor cells. Cells for imaging include cells that have been genetically modified (e.g., recombinant cells). Of particular interest is imaging of live cells, although the invention in some embodiments contemplates imaging of permeabilized or fixed cells. The cells are generally imaged in a sample comprising culture medium for cell maintenance and/or growth.

In many embodiments of the invention, particularly those that involve returning to the same field of cells and/or to the same individual cell in a field of cells, the cells are sufficiently immobilized on the substrate surface, e.g., are adherent to the substrate or to a treated substrate (e.g., coated with a cell-adhering substance), so that manipulation of the substrate does not result in movement of cells relative to the substrate. For example, the cell may adhere directly to the substrate, such as to tissue culture plastic (e.g., in a well), so that the cell position is relatively fixed with respect to the substrate, permitting manipulation of the substrate without dislodging the cell from its position relative to the substrate. This allows for return to precisely the same field of cells, including to the same individual cell within a field of cells.

In general, the invention provides for imaging at the single cell level, particularly living cells, which cells may be dispersed on a substrate surface as isolated single cells or contacting other cells (e.g., as in a monolayer), or which may be provided in a thin layer (e.g, as in a tissue slice). The cells imaged can be a homogenous or heterogenous cell populations (e.g., a mixed cell culture). Thus the invention provides for imaging of single cells, as well as cell populations, which cell populations may comprise cells of two or more different cell types.

The cells can be imaged with or without the aid of a detectable marker, such as a fluorescent label. Such detectable markers, and methods of associating such detectable markers with a cell, are well known in the art. Such detectable markers include fluorophores (or "fluors", which are referred to herein as exemplary without limitation), chemiluminescers, or other suitable detectable labels, including those for use in FRET (fluorescence resonance energy transfer) and BRET (bioluminescence resonance energy transfer) detection systems.

The systems and methods of the invention can provide for imaging of cell populations and individual cells, particularly over time, for observation of changes in cell viability (e.g., cell survival, cell health), cell physiology (e.g., synpatic physiology), signal transduction, organelle location and function, protein location and function (including interactions and turnover), enzyme activity, receptor expression and location, changes at cell surfaces, cell structures, differentiation, cell division; and the like. For example, in one embodiment, the systems and methods of the invention are used to determine whether the expression of a protein (e.g., the role of hungtingin in Huntington's disease), and appearance of changes in the levels or aggregation of the protein cause cell death or are instead a symptom of cell death (e.g., an attempt by the cell to avoid cell death, but which is not the cause of cell death itself). Of particular interest is the study of neurodegeneration of neurons in culture.

The systems and methods of the invention provide for imaging of single cells or populations of cells in real time and within desired time intervals, including relatively short time intervals. For example, a 24 well substrate, where each well comprises 13 contiguous optical fields to be captured by a CCD, can be imaged in approximately 10 minutes. In other instances, the time it takes to image cells will depend on the overall area to be covered, CCD resolution and the focus routine selected. In any case, data acquisition according to the present invention involves a mere matter of seconds (e.g., as little as about 1 to 3 seconds per field on average in the example) and less for actual imaging in view of time spent focusing and transitioning to the next location. While it may take up to about, 10–15 seconds to complete a focus step, it takes about 50 ms –1 second to collect an image of a field; the time to move from field to field is negligible. Therefore, from a time expenditure standpoint, imaging additional fields comes at virtually no cost where refocusing is not required.

The rapidity at which the cells can be imaged, for example in successive wells, and then re-imaged (e.g., by returning to the same field of cells, including the same individual cell) in a relatively short interval allows for observations that simply were not possible with conventional methods due to, for example, the length of time required to obtain each image. The invention also allows for tracking cell phenomena, such as cell functions of cells, cell survival, and the fate of individual cells in a population, over such relatively short time intervals. This is in contrast to conventional immunocytochemistry, which provides images taken only at a particular moment, which limit the amount of information obtained about progressive events (e.g., degeneration), and which are time-consuming (for example, analysis of a typical cell count of 300,000 cells in a neurodegeneration study took about 6 weeks to analyze; the invention allows for this same analysis to be completed in much less than half the time). Employing aspects of the present invention, it is possible to do in one hour of microscope and computer processing time what generally takes six full days for a person doing manual immunocytochemistry and microscopic analysis.

In addition, because the substrate can be removed from the system, subsequently replaced in the system, and the same cell populations and individual cells in the cell populations can be identified with precision, the systems and methods also provide for analysis of single cells and selected cell populations over long periods of time (e.g., on the order of hours to days to weeks or more).

The systems and methods of the invention also allow one to measure (either qualitatively or quantitatively) two or more biological variables, (e.g., cell function parameters or variables) at about or at the same time. For example, a cell can be imaged both by phase contrast and by fluorescence to provide information about changes in cell morphology and molecular events. In another example, the cell can be imaged using two or more detectable markers (e.g., two or more fluorescent markers).

The systems and methods of the invention also avoid user bias and variability of conventional systems by, for example, allowing one to obtain images of the same cell or population of cells in succession. In addition, the invention can be adapted for imaging cells that are sensitive to light or gross manipulation, e.g., the images can be obtained with comparatively little exposure to the light source and requiring only relatively fine movement of the substrate with which the cells are associated.

Kits. Kits for use in connection with the subject invention may also be provided. Such kits preferably include at least a computer readable medium including instructions and programming embodying or adapted to direct the functionality as discussed above. The instructions may include software installation or setup directions to program an otherwise ordinary microscope or cell scanner so as to function as described. The instructions may include directions for directing the microscope to perform as desired. Preferably, the instructions include both types of information.

Providing the software and instructions as a kit may serve a number of purposes. The combination may be packaged and purchased as a means of upgrading an existing microscope. The full program or some portion of it (preferably at least such code as defining the subject methodology—alone or in combination with the code already available) may be provided as an upgrade patch. Alternately, the combination may be provided in connection with a new microscope in which the software is preloaded on the same. In which case, the instructions may serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging), etc. In other embodiments, the instructions are present as an electronic storage data file present on a suitable computer readable storage medium, e.g., CD-ROM, diskette, etc., including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Of course, some form of access security or identification protocol may be used to limit access to those entitled to use the subject invention. As with the instructions, the means for obtaining the instructions and/or programming is generally recorded on a suitable recording medium.

Exemplary applications of the imaging systems and methods of the invention.

The imaging systems and methods of the invention find use in a variety of settings with a variety of different cells. The systems and methods of the invention also allow for following a cell or population of cells over any desired time interval, e.g., for a period of more than 2 hours, 5 hours, 12 hours, 24 hours, 2 days, 4 days, 6, days, 7 days, weeks and/or up to the life of a cell of interest in tissue culture. Imaging of the cell or other biological sample may occur at regular time intervals corresponding to those above or otherwise. The following are non-limiting examples of such, and further highlights certain advantages and features of the invention.

Imaging of cells so as to avoid or reduce phototoxicity. Phototoxicity is a major limiting factor in all forms of vital imaging and is directly related to the intensity, duration, and wavelength of incident light. The amount of incident light needed to detect a usable signal is minimized using the systems and methods of the invention. Phototoxicity can be a particular problem where one wishes to study slowly evolving processes, as the same samples of cells are subjected to light repeatedly The present invention significantly reduces phototoxicity in several ways. It is possible to focus the microscope using ultrashort exposures to low intensity white light and then to collect high-resolution fluorescence images using brief exposures to more intense light. Without automation, focusing is normally performed using continuous high intensity fluorescence light. Considering the time required to focus the microscope and then collect the image, the cells can be exposed to high-intensity phototoxic light for intervals that are an order of magnitude longer than with automation.

In addition, the methods of the invention that provide for ways to focus once but then acquire multiple adjacent fluorescence images without refocusing also help to reduce phototoxicity. This approach is an optimized way to collect a fluorescence image because the only significant light that most fields of cells receive is the light required to generate the image. Finally, because automation reduces substantially the duration of intense light exposure, less photobleaching occurs. Emitted fluorescence is brighter, reducing further the duration of excitation needed to generate a high resolution image.

Imaging of living cells for prolonged periods. Most living cells are grown on tissue culture plastic. During study of living cells, particularly in the context of slowly evolving processes, it is essential to maintain the health of the living cells (e.g., neurons) for time periods long enough to encompass the process under study. Ideally, cells will be the healthiest and least perturbed if they can be imaged briefly at regular intervals but in the same culture dishes in which they were originally grown. It is possible to image cells in tissue cultures dishes, under sterile conditions using an inverted microscope; however, an inverted microscope must image through the substrate (e.g., glass or plastic) that the cells are grown on. Compared to glass, tissue culture plastic transmits some wavelengths of light (e.g., ultraviolet) less well and can scatter more light, reducing image resolution. However, many cells, including neurons, survive longer and appear healthier when grown on tissue culture plastic than on glass, even when they are substrates are coated with polylysine and laminin to promote cellular attachment and differentiation. Thus, a goal of the present invention was to provide a system with optics that could generate high quality images through either plastic or glass.

Automatic acquisition of images through glass or plastic has important implications for the objectives that can be used. Immersion lenses generally gather more light than non-immersion (air) objectives. However, immersion lenses require immersion media, and the supply of this media is impractical for automatic imaging. Using a non-immersion lens to focus through substrates of different composition and thickness is also a problem. The refractive indices of these substrates vary one to another, and differ from the refractive index of the air through which the emitted fluorescence travels before being collected by the objective. Imaging through different refractive indices introduces chromatic and spherical aberration, which aberration increases with the numerical aperture of the lens. Aberration is noticeable at 20×, substantial at 40×, and almost insurmountable at 60×. Finally, some specimens such as cultured brain slices reside a relatively long distance away from the bottom of a tissue culture dish and the algorithms that automatically determine the plane of focus need to collect images from a variety of planes along the z-axis.

The use of objectives with very long focal lengths enables focusing on distant objects and prevents collisions between the objective and the tissue culture plate during automated focusing.

High throughput screening methods. The systems and methods of the invention find particular application in high throughput screening assays. Examples of such assays, without limitation, include identification of agents that elicit a desired response in a cell (e.g., modulation of cell death, receptor internalization, modulation (increase or decrease) of activity of signal transduction pathways, modulation of transcriptional activity, and the like) as well as analysis of nucleic acids of previously unknown or uncharacterized function (e.g., by introduction of a coding sequence of interest into a target cell for expression in the cell and analysis). Cells in which a response is observed may be referred to herein as "target cells", without any intended limitation as to the cell type, but rather as an indication of the cell affected by the agent.

In general, the systems and methods of the invention allow for analysis of the effect of agents in living cells, over desired time intervals, and with the same cell, which cell may be in a homogenous or mixed cell population. The assays of the invention can also examine the effects of agent-modified cells upon other cells in the culture, e.g., to examine the effect of expression of a nucleic acid agent in a target cell upon the target cell as well as other cells in the same well that may or may not be modified by the agent. For example, the assays of the invention can be used to detect "bystander effects" of a agent-modified cell upon cells not directly modified by the agent, where the latter cells may or may not be in physical contact with the agent-modified cell. In this context, the assays of the invention can be used to, for example, examine the effects of a secreted or cell surface protein encoded by or induced by the agent.

Detection of multiple variables in screening assays. Because the imaging systems and methods of the invention can be used to obtain data for multiple variables in a single sample. For example, one or more biologic variables can be detected, and, for example, changes in such biologic variables detected over time by comparing images obtained using the system of the invention.

For example, the systems of the invention can be used to analyze changes in a biological material over time, e.g., caused by contacting a material with an agent (e.g., increasing concentrations of an agent, adding additional agents, etc.), changing an environmental condition (e.g., modulation of temperature, osmolarity, etc.)). Changes in biological materials can be, for example, in the context of nucleic acid, accessibility of a detectable probe to a particular nucleic acid sequence, extent of supercoiling or double-strandedness, etc. In the context of protein, changes can include extent of protein folding, access of a probe to its binding site (e.g., detectable antibody or other protein-binding reagent), and the like.

For example, cell variables in a population of cells or in a single cell (e.g., one or more cell variables, two or more cell variables, and the like), the screening assays can involve assessing multiple cell variables in a single cell, which cell variables may optionally be assayed over different time intervals. In general, cell variables can be any detectable biological activity, cell component or cell product, particularly those which can be measured with sufficient accuracy and, preferably, can be detected in a manner compatible with a high throughput assay of the invention. Exemplary cell variables include, cell health (e.g., live-dead status as detected by cell membrane permeability to a dye such as trypan blue or ethidium bromide; induction of apoptosis, and the like); cell surface receptor status (e.g., receptor binding, activation, recycling, and the like); gene transcription levels (e.g., by detection of a reporter gene (e.g., GFP fusion protein)); cell differentiation (e.g., by detection of formation of cellular structures (e.g., dendrite formation in neural cells), presence or absence of cell differentiation antigens, and the like); transfection status (i.e., presence or absence of a recombinant polynucleotide for analysis in a target cell); and the like. Reference to "cell variable" throughout the specification is not meant to be limiting, but rather is recited for purposes of convenience and clarity only.

While most variables will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assay combinations, usually at least about 2 of the same assay combination will be performed to provide a value. Variability is expected and a range of values for each of the set of test variables will be obtained using standard statistical methods with a common statistical method used to provide single values.

The cell parameter to be analyzed is generally selected based on the following criteria, where any cell parameter need not have all of the criteria: modulation in the physiological condition that one is simulating with the assay combination; modulation by a factor that is available and known to modulate the parameter in vitro analogous to the manner it is modulated in vivo (e.g, as a control); associated with a response that is robust enough to allow for detection and can be differentiated from other cell variables to be analyzed; and in some instances, particularly in drug screening assays, changes in the parameter are indicative of toxicity leading to cell death.

Where more than one parameter is to be assessed, detectably distinguishable markers can be used to detect the different variables. For example, where the screening assay involves assessing the effect of a gene product encoded in a polynucleotide, one marker can be used to identify cells transfected with the construct of interest (e.g., by virtue of a detectable marker encoded in the construct containing the polynucleotide of interest or by virtue of a detectable marker present on a construct co-transfected with the construct of interest), while a second marker can be used to detect gene product expression (e.g, as in a detectable marker provided by a fusion protein produced from the gene product encoded by the polynucleotide). A third detectable marker can be used to assess the effect of the gene product upon the target cell (e.g., to assess cell viability, expression of a reporter gene under control of a promoter suspected of being regulated by a gene product of the candidate polynucleotide or by a factor regulated by a gene product of the candidate polynucleotide, and the like). In addition, information about cell morphology changes (e.g., cell differentiation, formation of cellular structures (e.g., dendrites)) can also be obtained through phase contrast images, which images can be aligned with and compared with, for example, fluorescent images on an individual cell basis, and over selected time intervals.

In another example, where the screening assay involved identification of agents that modulate activity of a receptor on the target cell, a first marker can be used to detect binding of the agent to the receptor, while a second marker can be used to detect transcriptional activation of a reporter gene. As used herein "detectable marker" includes molecules that, upon excitation at a given wavelength, provide for a detectable signal. In some embodiments, the same molecule may fulfill the role of multiple different markers in that the molecule has different excitation and/or emission wavelengths when the molecule is located in a different cellular compartment (e.g., molecules that have different emission wavelengths when present on the cell surface compared to when present in an acidic intracellular compartment).

Various methods can be utilized for quantifying the presence of the selected markers. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol 17(12):477–81).

Fluorescence technologies have matured to the point where an abundance of useful dyes are now commercially available. These are available from many sources, including Sigma Chemical Company (St. Louis Mo.) and Molecular Probes (Handbook of Fluorescent Probes and Research Chemicals, Seventh Edition, Molecular Probes, Eugene Oreg.). Other fluorescent sensors have been designed to report on biological activities or environmental changes, e.g. pH, calcium concentration, electrical potential, proximity to other probes, etc. Methods of interest include calcium flux, nucleotide incorporation, quantitative PAGE (proteomics), etc.

Multiple fluorescent labels can be used in the same assay, and cells individually detected qualitatively or quantitatively, permitting detection and/or measurement of multiple cellular responses simultaneously. Many quantitative techniques have been developed to harness the unique properties of fluorescence including: direct fluorescence measurements, fluorescence resonance energy transfer (FRET), fluorescence polarization or anisotropy (FP), time resolved fluorescence (TRF), fluorescence lifetime measurements (FLM), fluorescence correlation spectroscopy (FCS), and fluorescence photobleaching recovery (FPR) (Handbook of Fluorescent Probes and Research Chemicals, Seventh Edition, Molecular Probes, Eugene Oreg.). Of particular interest are those labeling techniques that are compatible with living cells and, where desired, with use over a desired time interval (e.g., comparison of images taken over a period of hours or of days).

Candidate agents. The term "agent" as used herein describes any molecule of interest that can be contacted with a living cell to assess the effect upon the living cell. Because of the high throughput abilities of the invention, a plurality of assay mixtures can be performed in parallel in different wells (e.g., in different wells of a multi-well plate) with different agent concentrations in order to examine the concentration-dependency of the observed effects. Typically, one of these concentrations serves as a negative control, i.e., at zero concentration or below the level of detection.

Candidate agents as used herein is meant to encompass numerous chemical classes, including, but not limited to, nucleic acids (e.g., DNA, RNA, antisense polynucleotides, and the like), polypeptides (e.g., proteins, peptides, and the like) organic molecules (e.g., small organic compounds having a molecular weight of more than 50 and less than about 2,500 daltons), ribozymes, and the like. Candidate agents can comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. As indicated above, candidate agents are also found among biomolecules including, but not limited to: polynucleotides, peptides, saccharides, fatty acids, steroids, purines, pyrimidines, derivatives, structural analogs or combinations thereof.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Polynucleotide as candidate agents. Where the candidate agent is a polynucleotide, the molecule can be a polymeric form of any length, either ribonucleotides or deoxynucleotides. Thus "polynucleotides" include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. Where the polynucleotide encodes a gene product, the polynucleotide may comprise intronic and exonic sequences.

The backbone of the polynucleotide can comprise sugars and phostphate groups (as may be typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. For example, antisense oligonucleotides are polynucleotides chemically modified from the native phosphodiester structure, in order to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs. The beta-anomer of deoxyribose may be used, where the base is inverted with respect to the natural alpha-anomer. The 2'-OH of the ribose sugar may be altered to form 2'-O-methyl or 2'-O-alkyl sugars, which provides resistance to degradation without comprising affinity.

Polynucleotides may comprise modified nucleotides, such a methylated nucleotides and nucleotide analogs, uracyl, other sugars, and linking groups such as fluororibose and thioate, and nucleotide branches. The nucleotide sequence may be interrupted by non-nucleotide components. A polynucleotide may be modified or further modified after polymerization, such as by conjugation with a labeling component to facilitate detection of the molecule. Other types of modification include, without limitation, caps, substitution of one or more of the naturally-occurring nucleotides with an analog, and introduction of means for attaching the polynucleotide to proteins, metal ions, labeling components, other polynucleotides or a support (e.g., a bead).

In one embodiment, discussed below in more detail, the polynucleotide is screened in the assays of the invention to assess the effect of a gene product encoded by the polynucleotide. In this embodiment, the polynucleotide can be provided in a construct adapted for expression of In this embodiment, the polynucleotide may be modified so as to operably link a promoter element to an open reading frame of the polynucleotide encoding a gene product so as to facilitate expression of the gene product in the target cell.

Polypeptides as candidate agents. In some embodiments, the candidate agent is a "polypeptide" or "protein", which terms are used interchangeably and which refer to a polymeric form of amino acids of any length, which can include genetically coded and non-genetically coded amino acids, chemically or biochemically modified (e.g., post-translational modification such a glycosylation or derivatized amino acids, polymeric polypeptides, and polypeptides having modified peptide backbones. "Polypeptides" that can be screened as candidate agents can include effusion proteins with heterologous amino acid sequence, fusion with heterologous and homologous leader sequences, with or without N-terminal methionine residues; immunologically tagged proteins; and the like. Polypeptide can also be modified to, e.g., facilitate attachment to a support (e.g, a bead). Where the polypeptide is not internalized into cells, the polypeptide may be introduced into a target cell by, for example, microinjection. Such may be less desirable, however, as microinjection manipulations may not be amenable to use in high throughput screening assays.

Cells for use in screening assays. Cells suitable for use in the screening assays of the invention include those described above. In some embodiments, it may be of particular interest to assays recombinant cells expressing a target gene product, and the assays adapted for detection of candidate agents that interact with the target gene product, e.g., by binding to, modulating expression of, or modulating a biological activity of the target gene product. "Target gene product" as used herein, and without intended limitation, refers to a protein or other gene product that is the focus of candidate agent screening. For example, the target gene product can be a receptor and the assay is adapted to identify agents that modulate an activity of the receptor.

General assay methods. Regardless of the goal of the screening assay, the assays involve contacting the agent and the cell, which may include introducing the agent into the cell, e.g., in the case of genetic agents, and detecting one or more cell variables. The change in cell parameter readout in response to the agent is measured, desirably normalized, and the parameter evaluated by comparison to reference readouts. The reference readouts may include basal readouts in the presence and absence of the factors, readouts obtained with other agents, which may or may not include known inhibitors of known pathways, etc. Agents of interest for analysis include any biologically active molecule with the capability of modulating, directly or indirectly, the cell parameter of interest of a cell of interest.

The agents are conveniently added to cells in solution, or readily soluble form, to the medium of cells in culture. The agents may be added in a flow-through system, as a stream, intermittent or continuous, or alternatively, adding a bolus of the compound, singly or incrementally, to an otherwise static solution. In an exemplary flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

In some embodiments, agent formulations do not include additional components, such as preservatives, that may have a significant effect on the overall formulation. Thus agent formulations can consist essentially of an agent to be tested and a physiologically acceptable carrier, e.g. water, cell culture medium, etc. In other embodiments, other reagents may be included in the screening assays, such as those to provide for optimal binding of agents to a binding partner, to reduce non-specific or background interactions, and the like. Such reagents should be, of course, selected so as to be compatible with screening of living cells.

As noted above, a plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Non-limiting examples of assays that take advantage of various aspects and features of the systems and methods of the invention are described below.

Drug screening assays. The imaging systems and methods of the invention can be adapted for use with a wide variety of assay formats to screen candidate agents for a desired biological effect upon a target cell (e.g., modulation of a cell parameter of interest), which biological effects have implications for use of the agent as a drug. For example, the agents can be assayed for modulation of cell differentiation, cell death (e.g., modulation of apoptosis), signal transduction (e.g., as in G-coupled protein receptors, GTP binding, detection of second messenger systems, etc.), ion channel activity (e.g., through assessing calcium influx, e.g., using calcium imaging), transcription (e.g., using reporter gene assays, e.g., to identify agents that affect expression of a target gene product), and the like. Of particular interest are those assays that are compatible for use with living cells.

In one embodiment, the screening assay can be a binding assay for detection of binding of a candidate agent to a binding partner in a cell, e.g., screening to identify agents that act as agonists or antagonist ligands for a receptor. In particular embodiments, the assay is a competitive binding assay, where the candidate agent is assessed for inhibition of activity of, for example, a known receptor ligand (e.g., a known agonist or antagonist). In this latter embodiment, the known ligand may be detectably labeled, so that, for example, a decrease in activity or binding of the known ligand is associated with a decrease in the detectable label of the known ligand.

Incubations of candidate agents with target cells are performed at any suitable temperature, typically between 4 and 40° C. Incubation periods are selected for optimum activity, but may also be optimized to facilitate rapid high-throughput screening. Typically between 0.1 and 1 hours will be sufficient; however, in some embodiments it may be desirable to assay the cells at selected intervals between these time points or for longer periods.

Functional genetic assays. In one embodiment, the imaging systems and methods of the invention are used to provide high throughput functional genetics screening assays. Such assays, in general, involve examining cells that have been genetically altered (e.g. by stable or transient introduction of a recombinant gene, or by antisense technology) to assess whether the genetic alteration results in a gain or loss in a biological function in the target cell. In addition to identification of agents that may be useful as drugs (e.g., as in gene therapy or antisense therapy), such assays are useful for, for example, identification of a gene of interest by virtue of the gain or loss of function, as well as analysis of genes of unknown function.

Methods for generating genetically modified cells are known in the art, see for example "Current Protocols in Molecular Biology", Ausubel et al., eds, John Wiley & Sons, New York, N.Y., 2000. The functional genetics assays in some embodiments can also serve as drug screening assays, where the candidate agent can be a polynucleotide, which polynucleotide can, for example, encode a gene product of interest (e.g., a peptide, protein, or antisense RNA), act as an antisense molecule, and the like. Exemplary "genetic agents" are described in more detail below. The genetic alteration may be a knock-out, usually where homologous recombination results in a deletion that reduction (e.g., to undetectable levels) of expression of a targeted gene; or a knock-in, where a genetic sequence not normally present in the cell is stably introduced.

A variety of methods may be used in the present invention to achieve a knock-out, including site-specific recombination, expression of anti-sense or dominant negative mutants, and the like. Knockouts have a partial or complete loss of function in one or both alleles of the endogenous gene in the case of gene targeting. Preferably expression of the targeted gene product is undetectable or insignificant in the cells being analyzed. This may be achieved by introduction of a disruption of the coding sequence, e.g. insertion of one or more stop codons, insertion of a DNA fragment, etc., deletion of coding sequence, substitution of stop codons for coding sequence, etc. In some cases the introduced sequences are ultimately deleted from the genome, leaving a net change to the native sequence.

Modification of cells for functional genetics assays. In general, functional genetics assays involve screening for the effect of addition or loss of function of a gene product through manipulation of a cell by introduction of a nucleic acid (e.g., by expression of a recombinant protein, antisense-mediated inhibition of expression, and the like). Such agents are referred to herein as "genetic agents" for convenience and without limitation. The introduction of a genetic agent generally results in an alteration of the total nucleic acid composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. In general, the effect of a genetic agent is to increase or decrease expression of one or more gene products in the cell.

Introduction of an expression vector encoding a polypeptide can be used to express the encoded product in cells lacking the sequence, or to over-express the product (e.g., to provide for an expression level greater than that associated with expression of the endogenous gene alone). Various promoters can be used that are constitutive or inducible. These coding sequences may include full-length cDNA or genomic clones, fragments derived therefrom, or chimeras that combine a naturally occurring sequence with functional or structural domains of other coding sequences. Alternatively, the introduced genetic agent may encode an anti-sense sequence; be an anti-sense oligonucleotide; encode a dominant negative mutation, or dominant or constitutively active mutations of native sequences; altered regulatory sequences, etc.

In addition to genetic agents having sequences derived from the host cell species, other genetic agents of interest can include, for example, genetic agents having sequences obtained from pathogens, for example coding regions of viral, bacterial and protozoan genes, particularly where the genes affect the function of human or other host cells. Sequences from other species may also be introduced, where there may or may not be a corresponding homologous sequence.

A large number of public resources are available as a source of genetic sequences, e.g., for human, other mammalian, and human pathogen sequences. A substantial portion of the human genome is sequenced, and can be accessed through public databases such as Genbank. Resources include the uni-gene set, as well as genomic sequences. For example, see Dunham et al. (1999) Nature: 402 489–495; or Deloukas et al. (1998) Science 282: 744–746. cDNA clones corresponding to many human gene sequences are available from the IMAGE consortium. The international IMAGE Consortium laboratories develop and array cDNA clones for worldwide use. The clones are commercially available, for example from Genome Systems, Inc., St. Louis, Mo. Methods for cloning sequences by PCR based on DNA sequence information are also known in the art.

In one embodiment, the genetic agent is an antisense sequence that acts to reduce expression of the complementary sequence. Antisense nucleic acids are designed to specifically bind to RNA, resulting in the formation of RNA-DNA or RNA-RNA hybrids, with an arrest of DNA replication, reverse transcription or messenger RNA translation. Antisense molecules inhibit gene expression through various mechanisms, e.g., by reducing the amount of mRNA available for translation, through activation of RNAse H, or steric hindrance. Antisense nucleic acids based on a selected nucleic acid sequence can interfere with expression of the corresponding gene. Antisense nucleic acids can be generated within the cell by transcription from antisense constructs that contain the antisense strand as the transcribed strand.

The antisense reagent can also be antisense oligonucleotides (ODN), particularly synthetic ODN having chemical modifications from native nucleic acids, or nucleic acid constructs that express such anti-sense molecules as RNA. One or a combination of antisense molecules may be administered, where a combination may comprise multiple different sequences.

In general, a specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene. A combination of sequences may also be used, where several regions of the mRNA sequence are selected for antisense complementation.

Dominant negative mutants can also be screened for generation of a loss of function in a cell, e.g., to facilitate analysis of protein function. These may act by several different mechanisms, e.g, mutations in a substrate-binding domain; mutations in a catalytic domain; mutations in a protein binding domain (e.g., multimer forming, effector, or activating protein binding domains); mutations in cellular localization domain, etc. General strategies are available for making dominant negative mutants (see for example, Herskowitz (1987) Nature 329:219, and the references cited above).

Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence. Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc. In mammalian host cells, a number of viral-based expression systems may be utilized, e.g., retrovirus, lentivirus, adenovirus, herpesvirus, and the like.

In cases where an entire gene, including its own initiation codon and adjacent sequences, is inserted into the appropriate expression vector, no additional translational control signals may be needed in order to accomplish expression in a target cell. However, in cases where only a portion of the gene coding sequence is inserted, exogenous translational control signals, including, perhaps, the ATG initiation codon, may need to be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

Use of techniques that provide for high efficiency of transfection (e.g., about 80–100% of cells may circumvent the need for using selectable markers to identify transfected cells. These may include adenovirus infection (see, for example Wrighton, 1996, J. Exp. Med. 183: 1013; Soares, J. Immunol., 1998, 161: 4572; Spiecker, 2000, J. Immunol 164: 3316; and Weber, 1999, Blood 93: 3685); and lentivirus infection (for example, International Patent Application WO000600; or WO9851810). Other vectors of interest include lentiviral vectors, for examples, see Barry et al. (2000) Hum Gene Ther 11(2):323–32; and Wang et al. (2000) Gene Ther 7(3):196–200.

In some embodiment, low transfection efficiency may be desired, e.g., where one wishes to examine the effects of transfected cells upon non-transfected cells, or where the detectable signal provided by multiple transfected cells makes accurate imaging of single cells difficult. Low transfection efficiency may be less than about 25%, 20%, 10%, or 5%, and even as low as less than about 1% of cells transfected. Because the imaging systems and methods of the invention allow for rapid identification and re-identification of the same cell, transfection efficiency is not critical to assessing the effects of genetic agents upon a target cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., lengths, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Selection and Detection—Simultaneous Measurement of Multiple Variables

To maximize the amount of information collected in a single experiment, the total number of independent variables that can be simultaneously measured and then related to cell (e.g., neuronal) function is maximized. The wavelength and intensity of light are two properties that can be used to resolve independent variables using the present invention. To this end, fixed multi-band pass dichroic mirrors and 10-position excitation and emission filter wheels were used to examine fluorescent signals from selected portions of the spectrum. A computer controls the filter wheels to coordinate their movements during automated image acquisition. A 14-bit charge-coupled device (CCD) camera was used to resolve a wide range of signal intensities for a particular band-width of light. Finally, the camera used to capture images was placed at the basement port of the inverted microscope to minimize the complexity of the light path, maximizing the number of emitted photons that are detected.

Figure 10:
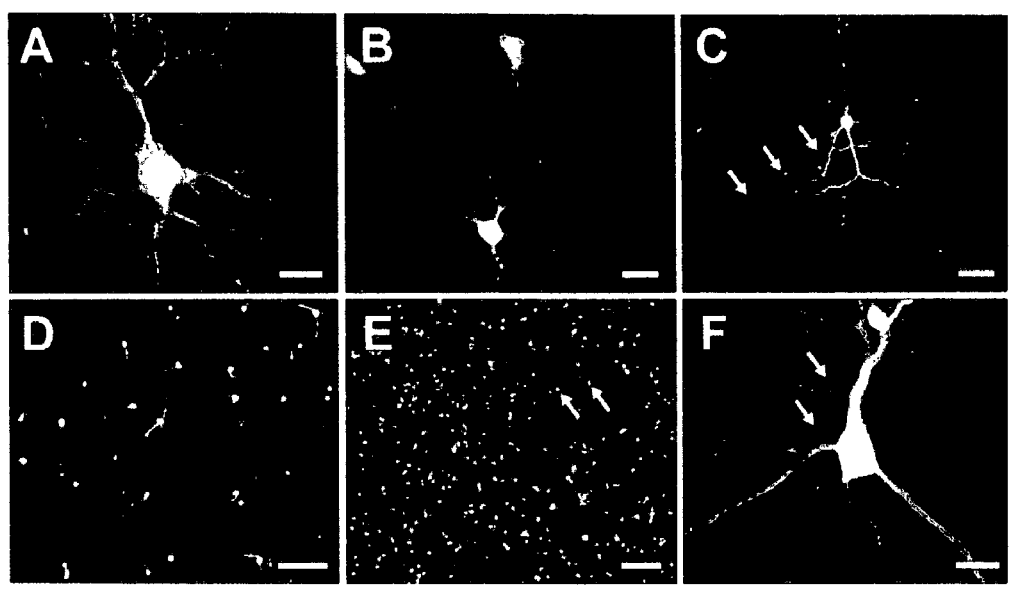
FIG. 10 is a panel of photographs (panels A–F) of highly resolved images of neurons grown on plastic tissue culture dishes expressing a variety of fluorescent proteins.

With this configuration, high-resolution images of neurons were obtained at various magnifications grown on plastic tissue culture with a variety of fluorescent proteins including cyan fluorescent protein, green fluorescent protein, yellow fluorescent protein, and dsRED (FIG. 10, Panels A–F). FIG. 10, Panel A is an image of hippocampal neuron transfected with dsRED collected with a 40×, N.A. 0.60 objective (scale bar=15 µm). FIG. 10, Panel B is an image of cortical neurons transfected with YFP collected with a 40×, N.A. 0.60 objective (scale bar=25 µm). FIG. 10, Panel C shows that the locations of growth cones and the paths of neurites can be traced (white arrows) on a striatal neuron transfected with GFP collected with a 20×, N.A. 0.45 objective (scale bar=50 µm). FIG. 10, Panel D shows that the full extent of the dendritic arbor of cortical neurons transfected with CFP can be seen with a 10×, N.A. 0.30 objective (scale bar=150 µm). FIG. 10, Panel E shows that cell bodies (white arrows) of cortical neurons transfected with GFP can be visualized with a 4×, N.A. 0.13 objective (scale bar=300 µm). FIG. 10, Panel F shows that spines can be visualized (white arrows) on dendrites of a cortical neuron transfected with GFP collected with a 40×, N.A. 0.60 objective (scale bar=15 µm).

Example 2

Automated Stage Movements and Focus with Low and High Numerical Aperture Objectives To automate image acquisition, the microscope was equipped with computer-controlled motorized stage and focus. To find the focal plane, software moves the focus knob to sample images at different positions along the z-axis. The image analysis software measures each image's overall spatial frequency by performing a fast Fourier transform. The image with the highest spatial frequency determines the focal plane. The motorized stage was used to determine the number of stepper motor movements needed to move the stage one complete microscope field in the four cardinal directions using 4×, 10×, 20×, and 40× objectives. Programs were then constructed that sequentially focus the microscope, move the desired excitation and emission filter wheels into place, capture an image, and then move the microscope to an adjacent non-overlapping field and repeat the sequence. According to the type of tissue culture plate, programs were written to efficiently scan portions of each well of a multi-well plate.

The present invention overcomes several obstacles. First, focusing using fluorescence had limitations. For example, the low transfection efficiency of the cells being observed meant that some fields lacked fluorescent objects on which to focus. In a doomed attempt to focus, the microscope would sometimes depart so far from the focal plane that it did not recover. Also, because fluorescence is a very inefficient process, intense illumination is often required to generate an acceptable signal. However, intense illumination can result in phototoxicity.

This problem was solved by using a separate low-intensity incandescent light source to generate a transmitted light image. With phase contrast optics, an image with sufficient spatial contrast was generated so as to sharply focus the microscope, whether or not a transfected fluorescent neuron was present in the field. In fact, this image contained so much spatial information that illumination could be limited to negligible levels (e.g., 20 millisecond light pulses at the lowest allowable rheostat setting) and continue to achieve focus reliably. Often, the focal plane is determined once per well and then used to calculate the correct Z-position of all the adjacent fields. Thus, exposure of each field to intense fluorescent light is typically limited to the single 20–500 ms pulse to collect an image. Two other obstacles were encountered in attempting to incorporate a purely adaptive focus routine into larger automated image acquisition programs. First, incorporating frequent automated focusing unacceptably slowed image acquisition routines. In an original approach, the automation program for controlling the microscope contained a sequential routine of automated focusing, fluorescence imaging, followed by a stage movement that was repeated for each new microscope field. This routine was to be used repeatedly in larger acquisition programs to collect stacks of images that collectively represent each field of cells neurons in each well of a multi-well tissue culture dish. However, an analysis of the operation revealed that automated focusing accounted for 90% of the time that it took to execute a cycle. After all, automated focusing itself is a multi-step process that involves image collection by the CCD chip of the camera, transfer of the electronic information from the chip to the computer, analysis of that information by the computer, and motorized movement of the focus knob in response to the image analysis. Of these steps, the transfer of the electronic information from the CCD chip to the computer is the most time-consuming step within the automated focusing routine.

The time required for transfer is directly related to the number of discrete detector elements on the CCD chip that collect emitted photons. The number and size of the elements also determine the spatial resolution of the image that the CCD chip can generate so it is usually desirable to use the whole chip to collect each image. However, the images that are used for automated focusing only need to have enough spatial resolution to find the focal plane and it was unclear whether the full spatial resolution of the chip was needed.

The effect of reducing spatial resolution of the image on autofocusing was tested by varying the number of discrete elements of the CCD chip accessed. The spatial resolution was reduced by reducing the portion of the CCD chip that accessed to the center quadrant of the chip, and then further reduced resolution by another factor of four by combining sets of four discrete elements within the quadrant. Despite the overall 16-fold reduction in spatial resolution, the automated focusing program reliably found the focal plane. However, an additional 2-fold reduction (32-fold total) in spatial resolution led to significant focusing failures. Reducing the spatial resolution 16-fold during autofocusing significantly increased the speed of the routine algorithm. Accordingly, employing autofocus hardware in such manner may be preferred in the present invention.

Yet another obstacle was encountered upon attempting to incorporate an efficient autofocusing algorithm into a larger program that imaged multiple microscope fields within a well. When the program was executed using a 20× objective (NA 0.45), over half of the images were out of focus. At least two reasons were discovered for the poor performance. The first involved an inherent limitation of phase contrast optics used to generate images for autofocusing. To acquire images of multiple fields of neurons within a single well of a multi-well dish, the stage was moved in a spiral pattern from the center of the well outward. However, the contrast degrades with increasing radial distance from the center of a well. Contrast degradation occurs because of the shape of the media meniscus in the well, and the effect that it has on the ability of phase contrast optics to generate the interference necessary to obtain contrast. Increasing the spatial resolution of the camera by using an image formed by the whole CCD chip did not help significantly.

Other common methods to generate contrast with transmitted light were considered. One method, differential interference contrast (DIC), is less susceptible to distorting effects of the meniscus compared with phase contrast optics; however, DIC cannot be used with plastic tissue culture plates. Use of such an approach is applicable to the invention, for example, where glass substrates are employed. Another strategy to generate contrast from transmitted light, Hoffman modulation optics, is compatible with plastic tissue culture plates. However, in preliminary experiments, these images contained less contrast than those generated with phase contrast optics and seemed to be less reliable for autofocusing. However, Hoffman optics may still be employed in the present invention.

Since problems were encountered when attempting to focus in the periphery of a well from a multi-well dish, focusing once per well was attempted, with collection of adjacent images within the same well without refocusing. It was hypothesized that if the plane formed by the cells within a well of the tissue culture plate is orthogonal to the axis of illumination and parallel to the plane of the detector, then focusing once should suffice because every other cell in that well should be at the same position along the z-axis. However, the bottom of the tissue culture plate was not perfectly orthogonal to the axis of illumination. Moreover, attempts to adjust the plate holder to align it proved to be both impractical and incompletely effective. Routine placement of the plate in the holder would lead to small but unpredictable deviations from the perfect orthogonal relationship and even with frequent time-consuming adjustments of the plate holder, 10–20% of the images remained out of focus.

Accordingly, two general solutions accounting for the practicalities of substrate placement were developed. One solution was to use an objective with a low numerical aperture. Lowering the numerical aperture increased the depth of field so that objects located along a wider range of z-axis positions nevertheless remained focused within an image. For example, it was discovered that a low magnification, low numerical aperture objective (e.g., 4×, N.A. 0.13) could be focused a single time in the center of a well from a 24-well plate. Then the adjacent microscope fields could be sharply imaged without refocusing. This configuration was ideal for high throughput cell counting because each low magnification field contained many cells. This configuration allowed for collection of images of additional fields within the same well without consuming time by refocusing.

For objectives with intermediate to high numerical apertures, a different solution was devopled. With increasing numerical aperture (e.g., 10×, N.A. 0.30; 20×, N.A. 0.45; 40×, N.A. 0.60), the depth of field narrows or becomes more shallow such that small differences in the z-position of cells, such as neurons, located in the center of a well compared to those located at the periphery now become resolved and only the neurons in the center of the well are sharply focused (assuming focus is originally set a the center of the well).

It was also discovered that the z-position of a cell within a well was largely determined by the overall tilt of the multi-well plate in the plate holder. Although the tilt varied slightly and unpredictably each time the plate was seated in the holder, its position generally remained constant during a single imaging session while it remained in the holder. Therefore, a program was developed that used automated focusing to empirically measure the tilt of the plate in the holder and then to use this measurement to automatically make precise adjustments to the focus position (z) according to the exact x-y position of a well or within a well. The program utilized provided for determining the precise z-position of the focal plane for four different x-y positions either within a single well or at the center of four different wells. With the exact x, y, z values for four different focal positions, the change in the focal plane (z) with a change in either x or y can be calculated. These values were incorporated into the automated focusing program such that the focal plane is empirically determined for the center position of each well and then the program automatically calculates the focal position for every other field within that same well. This strategy has enabled use of high numerical aperture lenses with automated acquisition programs, accurately focusing throughout the well and collecting images in a fraction of the time it would have in refocusing for each microscope field.

Example 3

Focusing for Different Wavelengths

Another problem became apparent during attempts to collect images of the same microscope field using different wavelengths of fluorescent light. Lenses refract different wavelengths of light by different amounts so the images formed from different wavelengths of emitted fluorescence were not focused exactly to the same point. The differences were small enough so that they were undetectable for low numerical objectives (e.g., 4×, N.A. 0.13). However, with increasing numerical aperture these differences could be resolved. Consequently, as the excitation and emission filters were changed, the objective had to be repositioned to keep images of the same microscope field sharply focused.

It was also discovered that the focal plane determined by automated focusing with transmitted light could be used as a reference to determine the position of the focal plane of fluorescence images. For a particular fluorophore, objective, excitation and emission filter set, the focal plane was located a relatively fixed distance from this reference focal plane. The location of the focal planes for different fluorophores relative to the reference focal plane was empirically determined, and then programs were developed that would automatically introduce the appropriate offset as the computer changed fluorescence filters.

Example 4

Precision and High-Throughput Image Acquisition

If the acquisition program was executed twice on the same plate without removing it from the plate holder, the duplicate images contained virtually identical microscopic fields. However, if the plate was removed and then replaced the plate on the holder between imaging sessions, the contents of the microscope fields from corresponding images only partially overlapped. The ability to find identical microscope fields in the first case but not the second suggests that the stage movements are very precise but that the position of the plate within the holder varies. Attempts to fix the position of the plate within the plate holder were impractical and largely ineffective.

The problem was instead solved by developing a simple program to relate the movements of the image acquisition programs to an internal reference point on the plate itself. For example, several manufacturers of multi-well plates stamp an alphanumeric designation next to each well on the underside of the plate. One of these stamps was used as a fiduciary mark for our program. In the program, the stage is directed to image the location of this fiduciary mark, autofocus, and then collect a reference image of the mark. Every other point in the acquisition program is related to this reference mark. When the plate is returned to the plate holder for another imaging session, the plate is repositioned to restore registration of the fiduciary mark with previous acquisition sessions and then the acquisition program is executed.

Figure 11A:
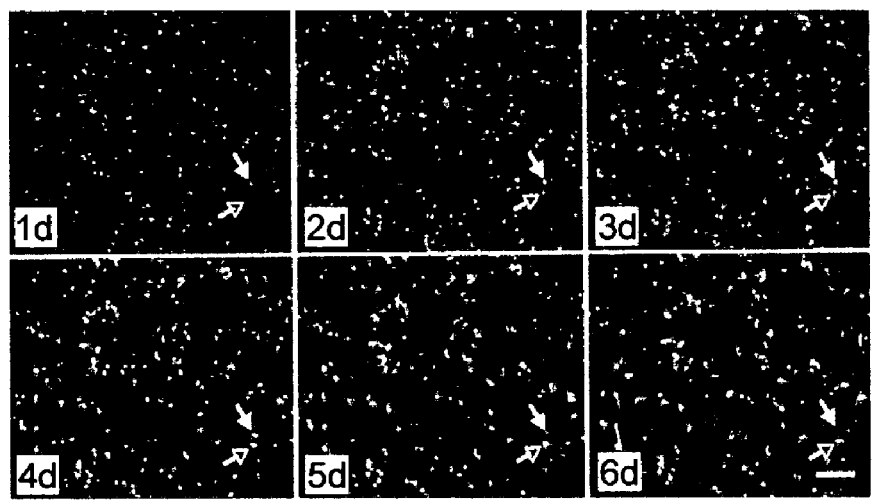
FIG. 11A is a panel of photographs of images collected (4×) at approximately daily intervals following transfection demonstrate the ability to return to the same field of neurons over arbitrary time intervals and to monitor their fates. One neuron (hollow white arrow) survives for the length of the experiment while another (solid white arrow) dies between the fourth and fifth days (scale bar=300 μm).
Figure 11B:
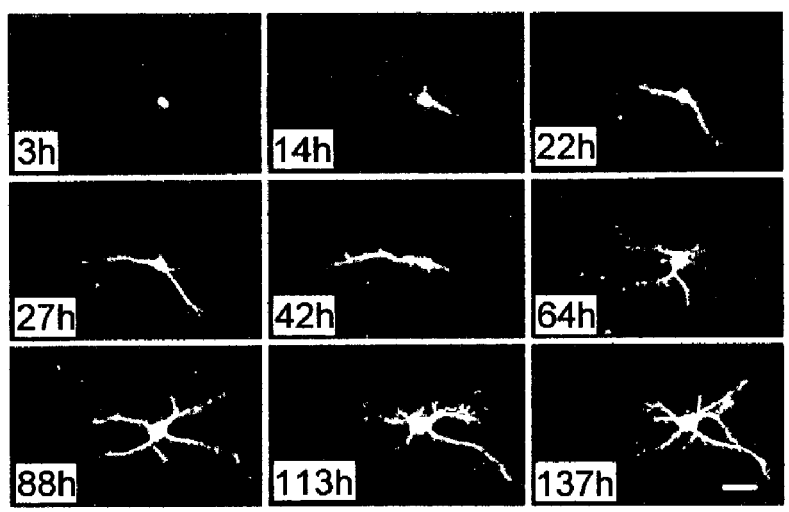
FIG. 11B is a panel of photographs of images similar to those in FIG. 11A, but collected using a higher magnification objective (20×), intracellular and extracellular structures (e.g., neurites) of single neurons can be resolved and monitored over time (scale bar=60 μm).

As shown in FIGS. 11A and 11B, this strategy was very successful, enabling us to return to precisely the same neuron or field of neurons over any desired interval (up to 6 days).

Example 5

Threshold Pixel Analysis

Having systematically scanned the tissue culture plate and acquired stacks of images, a two-step approach was applied to the initial stages of image analysis. First, a program was constructed that evaluates each pixel in an image and if its value exceeds some threshold number, the pixel is considered for further analysis. Next, contiguous supra-threshold pixels are grouped together as objects, which are further classified according to their geometry. In developing a method to determine the appropriate threshold value, it was desirable to have a method that was accurate, independent of user bias, amenable to automation, and so elegant that it would be possible to calculate the threshold value for an image from a list of its pixel values without knowledge of their spatial relationship or the need for complex models of their intensity distribution.

Initially, an attempt was made to calculate a threshold value for an image by determining the lowest pixel value within that image (i.e. the background) and then by adding some constant to that minimum value. However, light scattering from highly fluorescent objects distorted their boundaries by causing background pixels that were immediately adjacent to the true boundary of that object to receive enough light so that those pixels exceeded this calculated threshold. The error affected our ability to accurately measure the number and dimensions of objects.

Empirical examination was undertaken to determine whether other features of the image could be used to correct this error in our threshold calculation. It was discovered that the incorporation of some measure of the variance of the distribution of the pixels in the calculation led to a substantially more accurate prediction of the appropriate threshold value for most of our images.

Figure 12A:
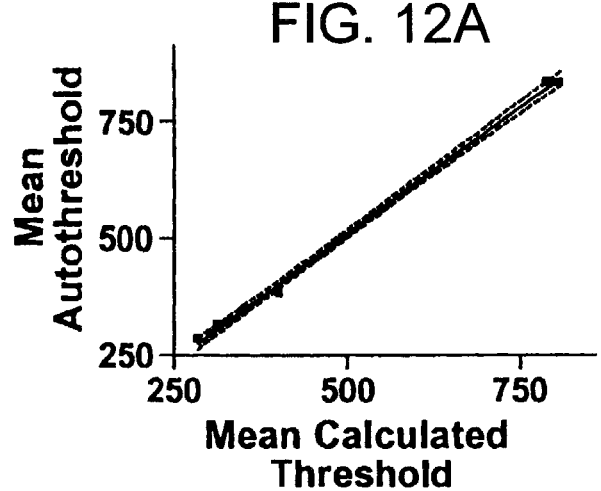
FIG. 12A is a graph comparing the performance of two algorithms designed to determine a threshold value for an image; a commercially available algorithm (the "Autothreshold algorithm") and an algorithm that was developed (the "Calculated algorithm").

A comparison of the simple program of the invention ("Calculated") to a commercially available algorithm (Universal Imaging, Inc.; "Autothreshold") is shown in FIG. 12A. Threshold values were determined by these two algorithms for nine sets of images of cortical neurons transfected with GFP. The two algorithms led to mean threshold values that were highly correlated ($r^2$=0.998), and were linearly related over a broad range of pixel intensity values (FIG. 12A).

Figure 12B:
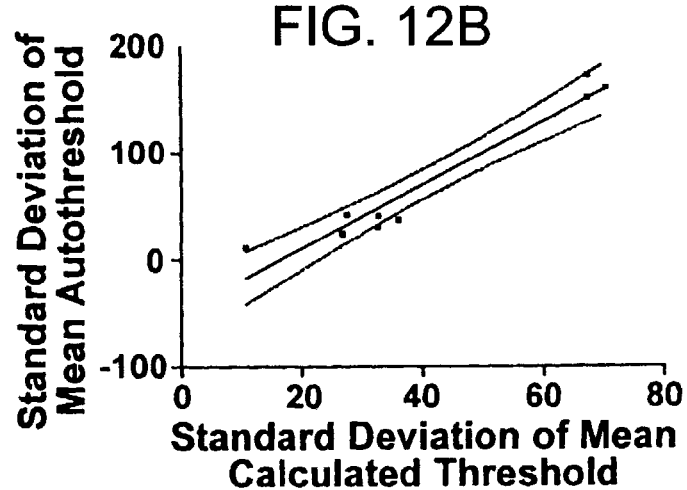
FIG. 12B is a graph comparing the variance associated with each algorithm by determining the standard deviation of the mean threshold values from FIG. 12A and by plotting the values derived from one algorithm against the other.
Figure 12C:
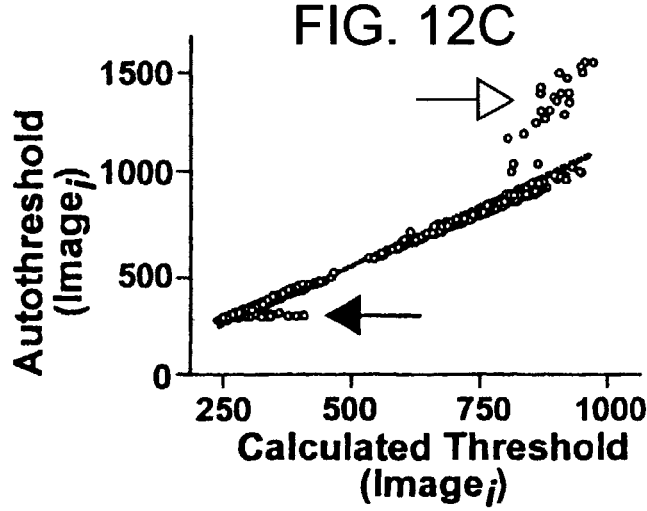
FIG. 12C is a graph plotting the threshold values for each of the 657 images in the nine sets used for FIG. 12A against those used for FIG. 12B.

FIG. 12B is a graph comparing the variance associated with each algorithm by determining the standard deviation of the mean threshold values from FIG. 12A and by plotting the values derived from one algorithm against the other. For the same set of images, the standard deviation associated with the Calculated threshold was approximately one-third the variance of Autothreshold ($r^2$=0.94). Thus, on an image-by-image basis, the variability in threshold value determination was generally less with the algorithm used in the invention than with the commercially available algorithm (FIG. 12B). FIG. 12C is a graph plotting the threshold values for each of the 657 images in the nine sets used for FIG. 300A against those used for FIG. 12B. In some images (about 5%), the two algorithms produced significantly different threshold values, indicated by two clusters of points that fall outside the 95% confidence intervals calculated from linear regression analysis of the distribution of points (solid arrow and hollow arrow).

Figure 13:
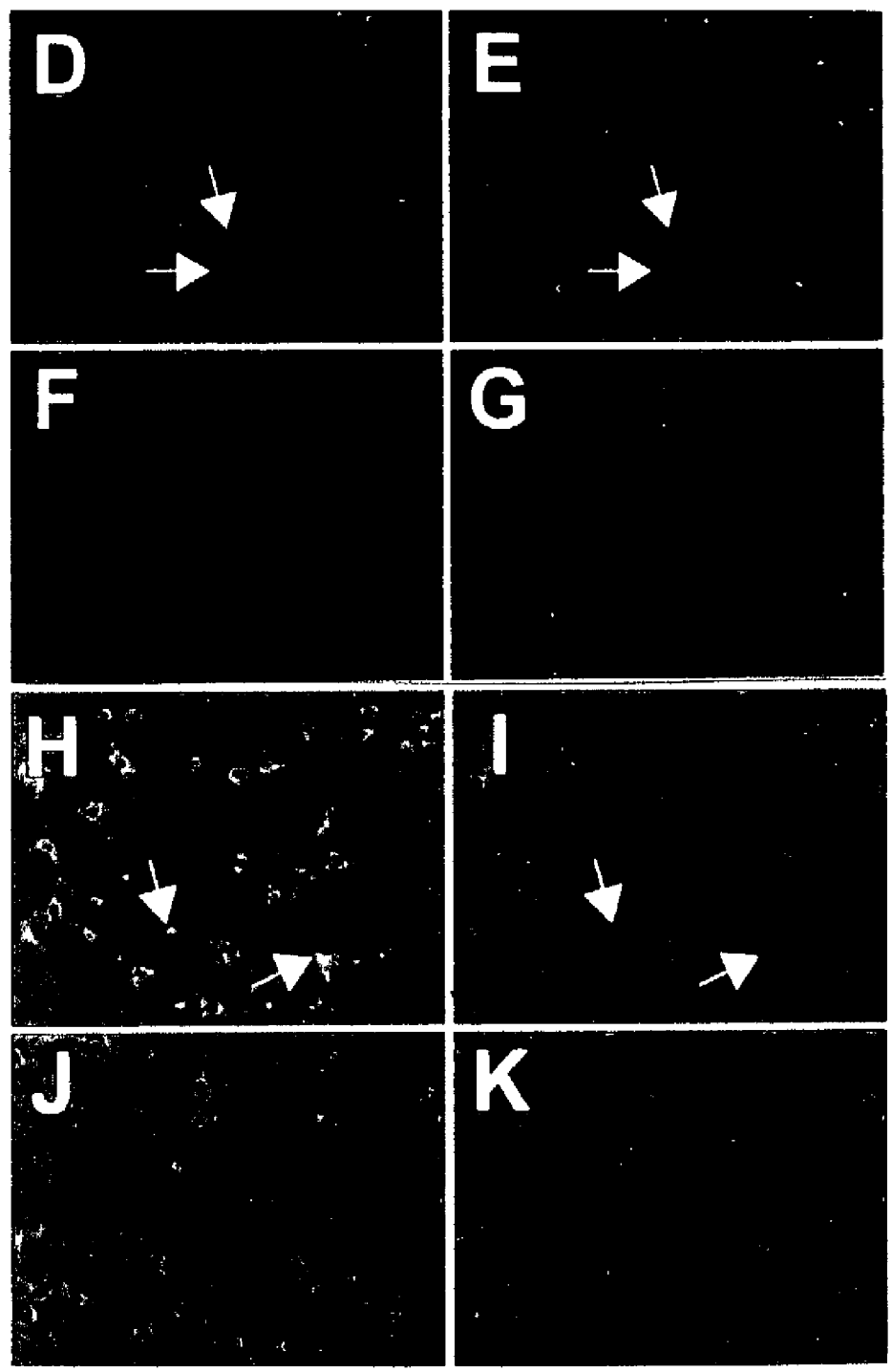
FIG. 13, Panels D–K are photographs of images from FIG. 12C that gave rise to discordant threshold values show that the Calculated algorithm is more accurate than the Autothreshold algorithm.

The difference in the performance could be attributed to errors made by the commercially available algorithm in approximately 5% of the images that were used for this comparison. FIG. 13, Panels D–K are photographs of images from FIG. 12C that gave rise to discordant threshold values and show that the Calculated algorithm according to the present invention is more accurate than the Autothreshold algorithm. Sample images from the first (FIG. 12C, solid arrow) and second (FIG. 12C, hollow arrow) discordant clusters were pseudocolored red to indicate which pixels exceed the threshold (FIG. 13, Panels D–E). Comparisons of images that produced discordant (D vs. E and H vs. I) or concordant (F vs. G and J vs. K) threshold values using Autothreshold (D,F) or Calculated threshold (E,G) algorithms shows that the discrepancy occurs because Autothreshold occasionally calculates a value that is either significantly too low (D) or two high (H). These errors can reduce the ability to detect neurons (white arrows, H vs. I) or the ability to resolve two neurons that have been detected (white arrows, D vs. E). These exemplary images show that errors in the commercially available algorithm tended to occur with images that contained objects whose fluorescence was either very bright or very dim.

Example 6

Analysis of Changes with Time

Figure 14A:
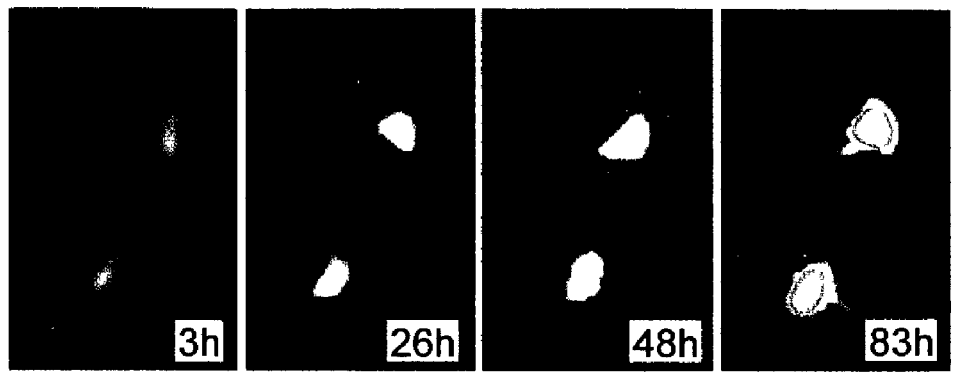
FIG. 14A is a set of photographs exemplifying that scaling threshold with expression of the marker gene makes it possible to track neurons over time.

The algorithm developed for selecting threshold values of unrelated images also accurately selected an appropriate threshold value for images of the same field of neurons at different points in time. This is important because fluorescence from the marker GFP gene can be detected within 2–3 hours after transfection and fluorescence continues to increase for the first 100 hours after transfection owing to increasing steady-state GFP levels. FIG. 14A is a panel of images of the same pair of neurons were acquired at different times following transfection. Although GFP expression increases significantly as indicated by the increasing brightness of the two neurons, the portion of the neuron (boundary area surrounding the brighter GFP singal) that exceeds the calculated threshold for each image remains relatively constant over this same interval.

Figure 14B:
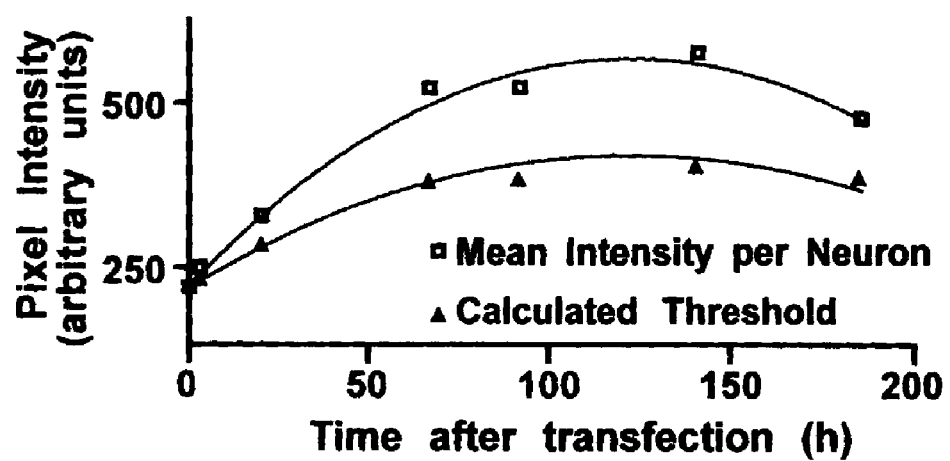
FIG. 14B is a graph of the results of a typical experiment, in which the mean pixel intensity of each neuron in an image increases significantly over the first 100 hours following transfection and the calculated threshold changes in parallel.

FIG. 14B is a graph of the results of a typical experiment, in which the mean pixel intensity of each neuron in an image increases significantly over the first 100 hours following transfection and the calculated threshold changes in parallel. Each point represents a mean value from 250–700 neurons. The portion of the neuron (e.g., soma or neurites) that exceeds threshold can be adjusted by modifying the algorithm.

By constructing the algorithm as a function of the variance in the distribution of pixel intensities, the calculated threshold value adjusts upward with increasing GFP expression (FIG. 14B). Compensation by the algorithm for the changing GFP expression levels enables the program to identify the same objects (e.g., neurons) from images collected at different time points (FIG. 14A). Compensation by the algorithm also makes it possible to more accurately measure the true dimensions of a neuron, independent of the absolute level of GFP (FIG. 14A). These properties of the algorithm make it possible to select the pixels from low magnification images that will be used for subsequent analysis in an automated manner and independent of user bias.

The algorithm arrives at a single number that is used to evaluate each pixel of the image. An important assumption is that the imaging system evenly illuminates the specimen and transmits any collected photons to the detector in a spatially uniform manner. Any spatial differences in illumination, collection, or transmission could artifactually increase or decrease the value of that pixel, causing it to exceed or undershoot the threshold. A Xenon arc lamp and fiber optic coupling was used to provide even and diffuse illumination. Low magnification objectives (4–10×) differed in the evenness of light transmission at the center of the microscope field compared with the edge and objectives with the least difference were used. Together, these modifications reduced the spatial inhomogeneity due to the imaging system to negligible levels (<2% of background across the field).

Once a cut-off was determined, contiguous pixels whose intensity exceeded this cut-off value were grouped together as distinct objects. The dimensions of these objects were evaluated empirically to determine the best variables for separating objects that represented individual neurons from objects that represented non-neuronal cells or debris. With low magnification objectives, and the threshold algorithm set to identify cell bodies, single neurons tended to have object areas that fell within a fairly narrow range. Computer filters were constructed that could routinely identify and measure 93–98% of the living neurons that were visible in a microscope field and which excluded >99% of fluorescent debris.

Example 7

Boolean Analysis, Acquisition of Images having Multiple Variables, and Analysis of Surrogate Expression in Functional Genetics Screening Assays One limitation of transient transfection approaches has been cell-to-cell variability of the expression of transfected genes. Cell-to-cell variability of steady-state expression levels could arise because the dose of the gene that each cell receives varies or because either the production or degradation of the protein encoded by the transfected gene varies. Since the biological response produced by a protein often depends critically on its concentration, failure to capture the relationship between the expression of that gene on a single cell level and the biological response that it produces could make it difficult to detect a relationship or significantly obscure the nature of that relationship. The cell-type heterogeneity inherent to the brain compounds these problems because the same gene may have significantly different effects that are both concentration- and cell type-dependent.

Therefore, it would be valuable to be able to both identify transfected cells and to estimate the expression of the transfected gene within each cell over time. Expression presumably predicts specific biological responses. Although the precise relationship may be complex, the nature of this relationship could be fully discovered by relating these two factors on a cell-by-cell basis. Use of marker gene expression to identify transfected cells (e.g., neurons) provides the potential for use of the expression of that marker gene as a surrogate for the expression of any co-transfected genes. Marker gene expression can then be used to relate expression of transfected genes to biological responses on a single cell level. Such an analysis would significantly increase the sensitivity of the assay and potentially reveal complex, non-linear relationships between gene expression and biological response.

Next, the expression level of a marker gene was tested for its use as a surrogate for the expression of a co-transfected gene. Neurons were co-transfected neurons with varying amounts of YFP and CFP, and the fluorescence of each protein measured in each neuron. The ability to correlate expression of one gene correlated with the expression of the other was then examined.

Figure 15A:
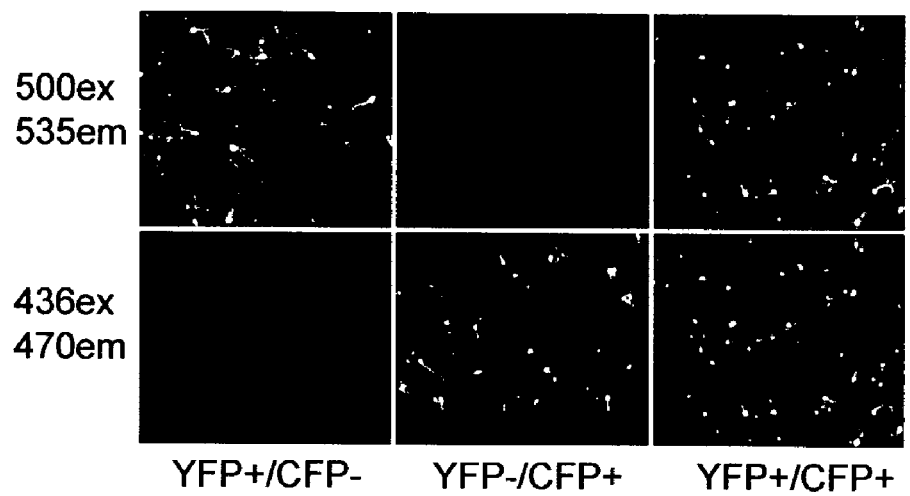
FIG. 15A is a set of photographs exemplifying application of BOOLEAN image analysis.
Figure 15B:
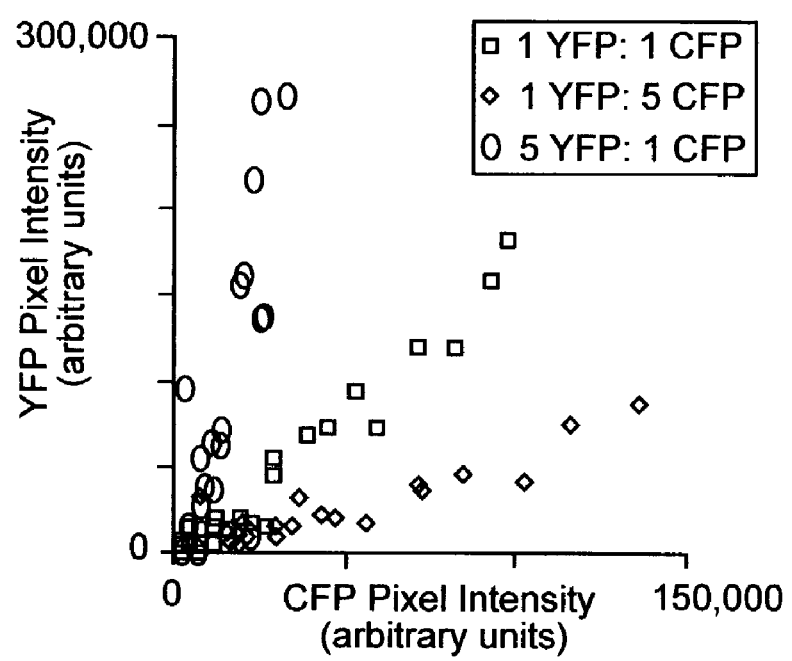
FIG. 15B is a graph showing cell-by-cell comparison of CFP and YFP fluorescence from neurons transfected with varying ratios of CFP and YFP.

Fluorescence of each protein was measured, and measurement of each was independent of the other (FIG. 15A). The neurons were then co-transfected with YFP and CFP constructs in varying ratios. The fluorescence of each protein was measured in each neuron. FIG. 15B shows the results of a cell-by-cell comparison of CFP and YFP fluorescence from neurons transfected with varying ratios of CFP and YFP. This comparison reveals that the co-transfection rate is essentially 100% and that the fluorescence intensity of one transfected protein is highly correlated with the other ($r^2=0.99$). Thus, although the expression of these two proteins varied significantly from cell-to-cell, the fluorescence of one protein was nearly always highly correlated with the fluorescence of the other ($r^2=0.99$) and related directly to the ratio of plasmid DNA that was used for transfection (FIG. 15B). Thus, the expression of a marker gene can be used to estimate the expression of a co-transfected gene, and the image acquisition system and methods of the invention can be used in the analysis of such cells.

The fluorescence of CFP to YFP was compared on a neuron-by-neuron basis. Automating these and other (e.g., BOOLEAN) comparisons accurately requires that the exact pixel positions between the two images correspond. However, the automated movements of the filter wheels occasionally led to a small misregistration of different fluorescence images of the same microscope field.

Therefore, a simple automated algorithm was developed to correct small misregistration errors. After each fluorescence image is collected, a 12-bit digital phase contrast image of the same microscope field is also collected. The phase contrast images were binarized in such a way to generate matrices in which approximately half the digits of each matrix are zeroes and half are ones. A subset of one matrix is selected and multiplied by a subset of the other matrix; the product matrix is summed and plotted. As discussed above in connection with FIG. 5, the sum of the product matrix reaches a maximum when the images (and the subset matrices that sample them) are identical (i.e., when they are in perfect registration).

Thus, by automating the process with a simple computer program, it is possible to empirically sample a set of potential X-Y misregistration quantities and to determine which portions of the original image are in optimal registration and can be used for direct comparisons.

Example 8

Monitoring of Cell Survival

Having demonstrated the utility of the system to rapidly image, identify, and quantify large populations of transfected neurons, and to return to the same microscope field repeatedly, the system was then applied to monitoring neuronal survival or long-term adaptive responses such as neurite or cell body growth. By comparing images collected periodically over several days or weeks, previous work found that GFP fluorescence of a neuron in one image would occasionally and abruptly disappear in a subsequent image. If the "loss" of GFP corresponded to the death of a neuron, that the loss of GFP positive neurons could be quantified over time as a measure of neuronal survival. To test whether the "loss" of GFP corresponded to the death of a neuron, the loss of GFP in transfected neurons was measured at the same time as the loss of membrane integrity using a membrane impermeant nuclear dye, ethidium homodimer (EtHD). EtHD staining of cell nuclei is taken as a positive sign of death in the widely used "LIVE-DEAD" assay.

Figure 16A:
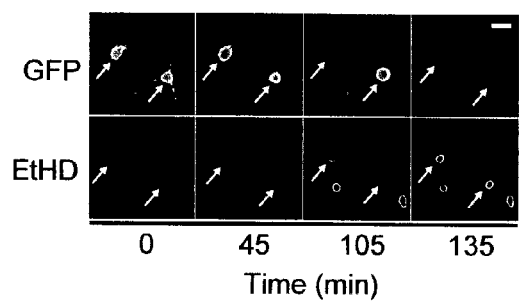
FIG. 16A is a panel of photographs exemplifying application of an automated imaging system to the study of neuronal survival, and showing that loss of GFP fluorescence correlates with a loss of membrane integrity and nuclear staining with ethidium homodimer (space bar=50 µm).

FIG. 16A is a panel of photographs exemplifying application of an automated imaging system to the study of neuronal survival, and showing that loss of GFP fluorescence correlates with a loss of membrane integrity and nuclear staining with ethidium homodimer. GFP transfected neurons (white arrows) were treated with the neurotoxin kainic acid (kainite) in the presence of the membrane impermeant nuclear dye, ethidium homodimer (EtHD). In response to the neurotoxin, kainic acid, and in the presence of extracellular EtHD, cell bodies of GFP transfected neurons rounded and swelled and their neurites began to retract. Between 60 (not shown) and 75 minutes, GFP fluorescence is abruptly lost from one neuron and its nucleus stains positively for EtHD. Later, the other transfected neuron in the image loses GFP fluorescence and stains positively for EtHD. EtHD appears to detect the nuclei of two other dead untransfected neurons in the image. Space bar=50 µm. Thus, overall, the GFP fluorescence of particular neurons disappeared eventually but abruptly, and at that same moment, the nuclei of those neurons stained positively with EtHD (FIG. 16A). Thus, the loss of GFP fluorescence correlated well with one widely accepted measure of cell death.

Figure 16B:
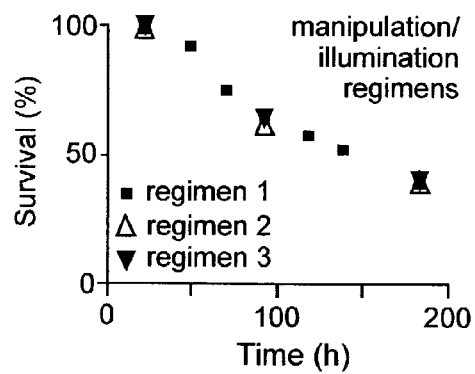
FIG. 16B is a graph showing that the frequency of automated imaging measurements does not detectably affect survival.

As a general approach for monitoring neuronal survival and other long-term adaptive or maladaptive responses, it would be important to know whether using GFP to mark transfected neurons or whether periodic imaging detectably affected neuronal survival. First, the survival of neurons from sister cultures were measured once a day, three times a week, or only once at the very end of the experiment, and compared. FIG. 16B is a graph showing that the frequency of automated imaging measurements does not detectably affect survival. The survival of transfected neurons in sister cultures was monitored with one of three different automated imaging regimens: (1) daily removal from the incubator and imaging; (2) daily removal from the incubator with imaging every third day or; (3) removal from the incubator and imaging every third day. Neurons subjected to these three regimens survived equally well. No significant difference in the number of transfected neurons between these groups was found, suggesting that our methods of imaging were not detectably affecting neuronal survival.

Next, expression of the transfection marker GFP was tested for its affect on survival. FIG. 16E is a graph showing the results of a parallel experiment, in which the survival of transfected neurons in two sister cultures was compared. One culture was imaged once at the end of the experiment (hatched bar) and the other was imaged both a day after transfection and at the end of the experiment (solid bars). The two cultures show nearly identical survival. Finally, if this approach is a valid way to measure neuronal survival, it should be able to detect the effects of molecules known to regulate survival. First, the ability to detect the neurotoxicity of kainic acid was tested. Neurons were transfected with GFP, either left untreated or treated with kainic acid, and periodically imaged before and after treatment. Stacks of images were subjected to automated analysis to determine the number of surviving neurons at any time point.

Figure 16C:
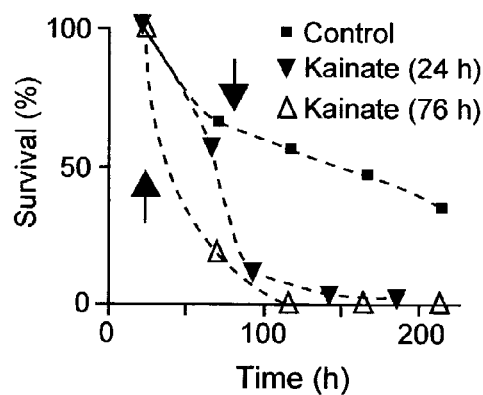
FIG. 16C is a graph showing that the automated imaging and analysis can be used to demonstrate kainate neurotoxicity.

FIG. 16C is a graph showing survival of transfected neurons in three sister cultures was monitored and compared. In the first (squares), neurons were left untreated. In the second (inverted triangles) and third (upright triangles), kainate was added 24 or 76 hours after transfection respectively. Automated imaging and analysis detected a significant decrease in neuronal survival in both kainate-treated cultures that closely followed kainate treatment.

Figure 16D:
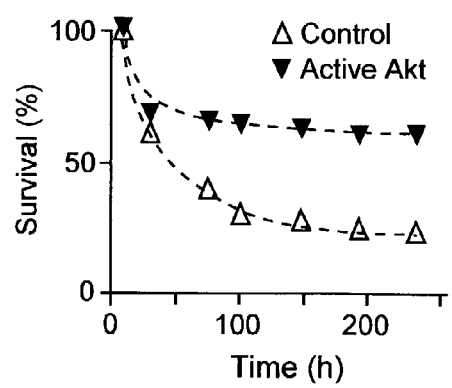
FIG. 16D is a graph showing that automated imaging and analysis detects the ability of constitutively active Akt to promote neuronal survival.
Figure 16E:
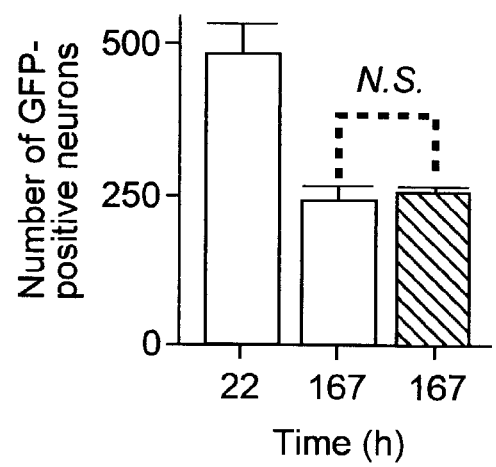
FIG. 16E is a graph showing that the expression of GFP does not detectably affect survival in an experiment where a first culture was imaged once at the end of the experiment (hatched bar) and the other was imaged both a day after transfection and at the end of the experiment (solid bars).

FIG. 16D is a graph showing that automated imaging and analysis detects the ability of constitutively active Akt to promote neuronal survival. Neurons were transfected with GFP along with either an expression plasmid for a constitutively active form of Akt (inverted triangles) or an empty control vector (upright open triangles).

Thus, overall, kainic acid induced a significant decrease in neuronal survival as measured by GFP positive neurons (FIG. 16D). Conversely, co-transfection of a constitutively active form or the pro-survival kinase Akt led to a significant increase in neuronal survival (FIG. 16E). Taken together, these results suggest that the automated microscope is a sensitive and valid way to measure the effects of extracellular or intracellular molecules on neuronal survival.

Example 9

Monitoring of Survival of Individual Neurons

The ability to return to precisely the same microscope field at periodic intervals and monitor the survival of individual neurons creates additional opportunities for data analysis. For example, the well-established method of Kaplan-Meier analysis can be applied to quantify the survival-promoting effects of Akt from analysis of data using either low magnification objective (and thus a larger number of cells in the field and thus the image—referred to here as a "population-based" analysis) or a high magnification (and thus a lower number of cells in the field and thus the image referred to here as a "single cell-based" analysis).

At low magnification (4×) used for population-based analysis, about 50–500 neurons per field (e.g., about 100 to about 400, about 150 to 350 or about 300 neurons per field) were observed. Single cell-based analysis was performed about at high magnification (20×), which allows for spatial resolution of changes within a neuron (e.g., the formation of an inclusion body, the change in the morphology of a dendrite, etc.), and provides for observation of about 10–100 neurons per field (about 15 to about 75, about 20 to 50 or about 30 neurons per field). Single cell-based analysis was performed in this example by analyzing every neuron in 3 random images followed longitudinally (i.e., images were taken a selected times or over selected periods). Application of Kaplan-Meier analysis (which is fundamentally a longitudinal analysis of individual objects) is justified since, in each instance, one returns to the same microscope field and "deduces" the number of individual neurons that have been lost during the interval.

Automated analysis was first used to choose a particular field and monitor the number of neurons in that field at each measurement interval. Since these neurons were post-mitotic, the number of neurons in a field at one time point was subtracted from the number in that field at the preceding time point to deduce the number of neurons that had died sometime during the intervening period. For the purposes of survival analysis and by convention, neurons that died during the interval were assigned an event time equivalent to the period from transfection to the time when they first disappeared from an image.

Figure 17A:
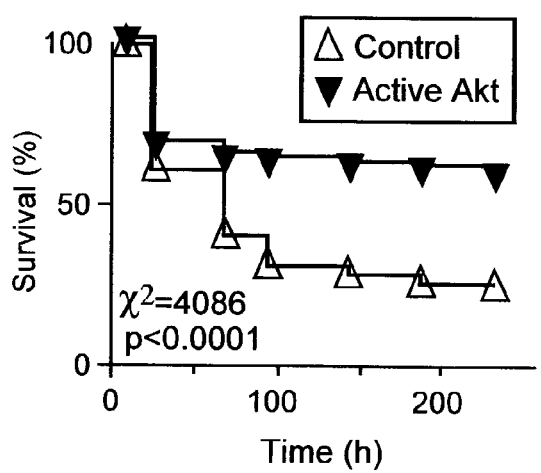
FIG. 17A is a graph showing results from Kaplan-Meier analysis of population-based Akt survival data.
Figure 17B:
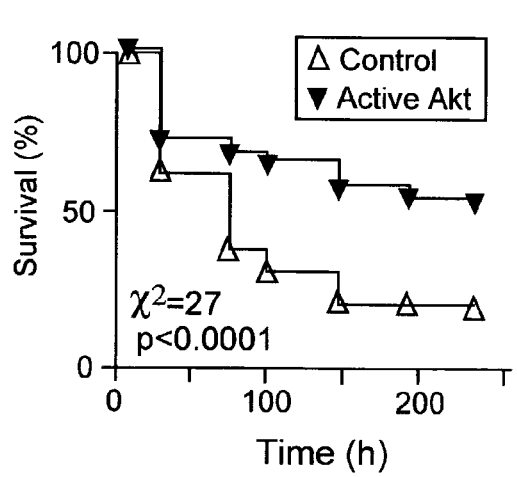
FIG. 17B is a graph showing results of Kaplan-Meier analysis of single-cell-based Akt survival data.

Single cell analysis data was obtained from images of 3 cells in a field of about 300 cells. FIGS. 17A and 17B are graphs showing the results of Kaplan-Meier analysis of population-based (FIG. 17A) and a single cell-based (FIG. 17B) study of Akt survival data. In each case, the approaches were extremely sensitive and detected a highly significant survival promoting effect of Akt.

Statistical analysis for each of the curves is shown in each of FIGS. 17A and 17B demonstrated the validity of both the population-based and single cell-based approaches. The chi square values for each are extremely high. From this, it is evident that the automated analysis provided by the imaging system of the invention provides both speed and independence of user bias. In addition, the imaging system provides extraordinary sensitivity for detecting and quantifying even small differences in an image field. Without being held to theory, this sensitivity comes from at least two sources. First, the automation provide for analysis of very large numbers of cells (e.g., 31,000 neurons in the Akt example here), which provides for increased statistical power. Second, the additional information derived from longitudinal analysis (i.e., analysis over time) is extracted by Kaplan-Meier curves and translated into additional sensitivity. Longitudinal analysis detects important differences, the magnitude and even existence of which might change with time such that they might be missed or underestimated by single snap shots.

In addition, even though single cell analysis produces a chi-square that is much smaller (presumably related to the numbers since the qualitative difference looks similar), the statistical significance is still quite valid, and in fact is at the limit of what conventional statistical programs can detect.

Other statistical analyses, such as Cox Proportional Hazard Regression analysis, can be applied to data from analysis of single cells. Cox Proportional Hazard Regression analysis can be used to identify which time-varying quantities predict a particular biological or pathobiological outcome, how strongly they predict the outcome, and to what extent the factor works alone or in combination with other factors.

Claims

While the present invention has been described with reference to the specific embodiments thereof, it should be understood by those skilled in the art that various changes may be made and equivalents may be substituted without departing from the true spirit and scope of the invention. It should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. It is to be understood that the breadth of the present invention is to be limited only by the literal or equitable scope of the following claims.

I claim:

1. A method for imaging biological material, comprising:
    positioning a substrate in association with an objective of an inverted microscope, said substrate having a plurality of discrete regions and an optically detectable reference mark thereon;
    determining a location for a cell in a population of cells positioned within at least one of said discrete regions with respect to a location of said reference mark and storing location information for said at least one discrete region in a computer memory;
    imaging said cell in said at least one of said discrete region to generate first image information;
    storing first image information for said cell in said at least one discrete region;

returning to the location of the imaged cell within said at least one discrete region by alignment with said reference mark; and imaging said cell within at least one discrete region to generate second image information and aligning said second image information with said stored first image information.

2. The method of claim 1, wherein each discrete region is a well of a multi-well plate.

3. The method of claim 1, wherein said aligning is achieved by maximizing the sum of the product of at least a portion of a matrix of pixel values from said first image information and at least a portion of a matrix of pixel values from said second image information.

4. The method of claim 3, wherein said matrices are provided so that pixel values below a threshold level are assigned the value of zero.

5. The method of claim 4, wherein pixel values above said threshold level are assigned the value of one.

6. The method of claim 1, further comprising:
contacting said biological material in a well of a multi-well plate with a candidate agent;
said first image information and said second image information being obtained at a time interval sufficient to allow for interaction of the candidate agent with said biological material; and
comparing said first and second image information to assess the effect of said candidate agent upon said biological material.

7. The method of claim 1, wherein said aligning of said second image information with said stored first image information comprises:
generating a first matrix of image values from said first image information;
generating a second matrix of image values from said second image information; and
aligning said first and second images by first using said reference mark and then by maximizing the sum of the product of at least a portion of said first and second matrices of image values.

8. The method of claim 7, wherein said alignment is performed using phase contrast images.

9. The method of claim 7, wherein a first set of fluorescent image results for said biological material is obtained and said aligning is performed prior to obtaining a second set of fluorescent image results for said biological material.

10. The method of claim 9, wherein said fluorescent images are of different colors.

11. The method of claim 7, wherein said aligning is performed using fluorescent images.

12. The method of claim 7, wherein the method further comprises:
contacting said biological material with a candidate agent;
said first and second images being obtained at a time interval sufficient to allow for interaction of the candidate agent with said biological material; and
comparing image information of the aligned images to assess the effect of said candidate agent upon said biological material.

13. The method of claim 1, wherein said imaging to generate said first or second image information comprises:
determining a slope of said substrate on said microscope by focusing on at least three points of or on said substrate;
determining a focus setting for a portion of an area; and
imaging said area with focus settings adjusted to account for said substrate slope.

14. The method of claim 13, wherein said substrate comprises a plurality of wells and said area is a well.

15. The method of claim 14, wherein focusing occurs for each of said plurality of wells a single time prior to imaging.

16. The method of claim 14, wherein said determining of slope is performed by focusing on said biological material within one well.

17. The method of claim 13, wherein said determining of slope is performed by focusing on said biological material.

18. The method of claim 1, wherein said imaging to generate said first image information and to generate said second information comprises:
imagine with an automated optical system adapted to detect at least two spectral ranges, wherein said imagine detects;
a first spectral range;
switching said system to detect a second spectral range; and
adjusting focus of an objective of said system using a predetermined setting to compensate focus for detection of said second spectral range.

19. The method of claim 18, wherein said substrate defines a multi-well plate.

20. The method of claim 18, wherein said spectral ranges are selected from the group consisting of fluorescent emissions, luminescent emissions, chemiluminescent emissions, and reflected light.

21. A method of analyzing image data of biological material associated with a substrate, comprising:
imaging said biological material with a computer controlled system to obtain image results, said biological material being labeled with at least one fluorophor, said image results being represented by a plurality of pixel values;
calculating a mean threshold value of said pixel values;
calculating a standard deviation of said mean threshold value; and
comparing said image pixel values to a threshold value determined by a line equation having a slope and a y-intercept,
wherein said mean threshold value is the slope and the y-intercept comprises a minimum pixel value of said image results, and wherein pixel values below said threshold are disqualified, the remaining pixel values being qualified.

22. The method of claim 21, wherein groups of adjacent qualified pixel values are classified into objects using a geometric filter.

23. The method of claim 22, wherein a count of classified objects is performed and recorded by said system.

24. The method of claim 1, wherein:
said first image information is generated at a first time point and said second image information is generated at a second time point; and
said aligning is accomplished in reference to a location of said reference mark and maximizing the sum of the product of two matrices corresponding to at least part of said first and second images.

25. The method of claim 24, further comprising;
contacting said cell with a candidate agent; and
comparing said first and second images to assess the effect of the candidate agent upon said cell.

26. The method of claim 25, wherein said contacting is after obtaining said first image and prior to obtaining said second image.

27. A method for identifying a candidate agent having a biological activity of interest, the method comprising:

contacting biological material with a candidate agent for a period sufficient to allow for interaction of the candidate agent with said biological material, wherein said biological material associated with a well of a substrate, which substrate has a reference mark;

obtaining a first image of said biological material at a first time point;

returning to said biological material at a second time point and obtaining a second image of said biological material, wherein said returning is accomplished using the reference mark and maximizing the sum of the product of two matrices corresponding to said first and second images so as to provide for alignment of the first and second images of said biological material; and comparing the aligned first and second images, wherein differences between the first and second images are indicative of the biological activity of the candidate agent.

28. The method of claim 27, wherein the first and second images are of a detectable marker indicative of the same biologic variable so that the difference between the first and second images are indicative of a change in the same biologic variable.

29. The method of claim 27, wherein the first image is of a detectable marker indicative of the state of a first biologic variable and the second image if of a detectable marker indicative of the state of a second biologic variable.

30. A method for identifying a candidate agent having a biological activity of interest, the method comprising:

contacting biological material with a candidate agent for a period sufficient to allow for interaction of the candidate agent with said biological material, wherein said biological material is associated with a discrete region of a substrate, which substrate has a reference mark;

obtaining at a first time point an image of said biological material to detect a first biologic variable and an image of said cell to detect a second biologic variable;

returning to said biological material at a second time point and obtaining images to detect said first and second biologic variables, wherein said returning is accomplished using said reference mark and maximizing the sum of the product of matrices corresponding to at least said first and second images of one of said first and second biologic variables so as to provide for alignment of the images of the biological material; and comparing the aligned first and second images of each of said first and second biologic variables, wherein differences between said first and second images are indicative of the biological activity of the candidate agent.

31. An automated microscopy system programmed to operate according to a method selected from the methods of claim 1, 7, 13, 18, 21, 24, 27 or 30.

32. A computer-readable medium containing data representing image results produced in connection with a method chosen from the methods of claim 1, 7, 13, 18, 21, 24, 27 or 30.

33. A computer-readable medium comprising at least a portion of a program to direct an automated microscopy system to perform a method selected from the claim 1, 6, 7, 12, 13, 18, 21, 24, 27 or 30.

34. The computer-readable medium of claim 33, wherein the entirety of said program is provided.

35. A kit comprising the computer readable medium of claim 33 in packaged combination with instructions for use with the same.

36. The method of any of claims 1, 12, 13, 18, 21, 27 or 30, wherein said biological material comprises a cell.

37. The method of claim 7, wherein the sample is a cell of a population of cells on the substrate.

38. The method of claim 17, wherein said biological material is a cell of a population of cells.

* * * * *